(12) United States Patent
Shin

(10) Patent No.: US 12,402,920 B2
(45) Date of Patent: Sep. 2, 2025

(54) ENDOSCOPIC INTERSPINOUS INSERT

(71) Applicant: Sung Joon Shin, Incheon (KR)

(72) Inventor: Sung Joon Shin, Incheon (KR)

(*) Notice: Subject to any disclaimer, the term of this patent is extended or adjusted under 35 U.S.C. 154(b) by 242 days.

(21) Appl. No.: 17/923,238

(22) PCT Filed: May 6, 2021

(86) PCT No.: PCT/KR2021/005646
§ 371 (c)(1),
(2) Date: Nov. 4, 2022

(87) PCT Pub. No.: WO2021/225374
PCT Pub. Date: Nov. 11, 2021

(65) Prior Publication Data
US 2023/0157733 A1 May 25, 2023

(30) Foreign Application Priority Data
May 7, 2020 (KR) ........................ 10-2020-0054196

(51) Int. Cl.
*A61B 17/70* (2006.01)
(52) U.S. Cl.
CPC ................ *A61B 17/7065* (2013.01)
(58) Field of Classification Search
CPC .................................................. A61B 17/7065
See application file for complete search history.

(56) References Cited

U.S. PATENT DOCUMENTS

| | | |
|---|---|---|
| 2002/0026244 A1 | 2/2002 | Trieu |
| 2002/0029039 A1* | 3/2002 | Zucherman ........ A61B 17/7068 606/279 |
| 2005/0261768 A1 | 11/2005 | Trieu |
| 2006/0004447 A1 | 1/2006 | Mastrorio et al. |
| 2007/0203497 A1 | 8/2007 | Zucherman et al. |

(Continued)

FOREIGN PATENT DOCUMENTS

| | | |
|---|---|---|
| JP | 4860691 B2 | 1/2012 |
| JP | 5132519 B2 | 1/2013 |

(Continued)

OTHER PUBLICATIONS

Korean Notice of Allowance dated Sep. 14, 2023 issued on Application No. 10-2023-0001302.

*Primary Examiner* — Julianna N Harvey
(74) *Attorney, Agent, or Firm* — Invenstone Patent LLC

(57) ABSTRACT

Disclosed is an endoscopic interspinous insert capable of being inserted into a body through an incision hole during a spinal endoscopic operation. The endoscopic interspinous insert includes a first support member including a first support body configured to support any one of the adjacent spinous processes, and a plurality of first support protrusions protruding from two opposite ends of the first support body, a second support member including a second support body configured to support the other of the adjacent spinous processes, and a plurality of second support protrusions protruding from two opposite ends of the second support body, and an adjustment member disposed between the first support member and the second support member and configured to adjust a distance between the first support member and the second support member.

3 Claims, 28 Drawing Sheets

(56) References Cited

U.S. PATENT DOCUMENTS

| | | | | |
|---|---|---|---|---|
| 2008/0294200 A1* | 11/2008 | Kohm | ................ | A61B 17/7062 |
| | | | | 606/279 |
| 2010/0106190 A1* | 4/2010 | Linares | .............. | A61B 17/7067 |
| | | | | 606/249 |
| 2011/0218572 A1* | 9/2011 | Lechmann | ......... | A61B 17/7065 |
| | | | | 606/279 |
| 2012/0253395 A1 | 10/2012 | Linares | | |
| 2023/0130877 A1* | 4/2023 | Linares | .............. | A61B 17/7065 |
| | | | | 606/248 |
| 2023/0136415 A1* | 5/2023 | Linares | .............. | A61B 17/8605 |
| | | | | 606/247 |
| 2023/0233332 A1* | 7/2023 | Linares | .............. | A61B 17/7065 |
| | | | | 606/246 |
| 2023/0233333 A1* | 7/2023 | Linares | ................ | A61F 2/4405 |
| | | | | 623/17.16 |
| 2023/0240726 A1* | 8/2023 | Linares | .............. | A61B 17/7065 |
| | | | | 606/249 |
| 2023/0320864 A1* | 10/2023 | Linares | ................ | A61F 2/4611 |
| | | | | 606/247 |

FOREIGN PATENT DOCUMENTS

| | | | |
|---|---|---|---|
| KR | 10-2009-0096609 A | 9/2009 | |
| KR | 10-1010306 B1 | 1/2011 | |
| KR | 10-2014-0077183 A | 6/2014 | |
| KR | 10-1661635 B1 | 9/2016 | |
| KR | 10-1719290 B1 | 4/2017 | |
| WO | 2020-070697 A1 | 4/2020 | |

* cited by examiner

ENDOSCOPIC INTERSPINOUS INSERT

CROSS-REFERENCE TO RELATED APPLICATIONS

This application is a National Stage filing under 35 U.S.C. 371 of International Application No. PCT/KR2021/005646, filed on May 6, 2021, which claims the benefit of earlier filing date and right of priority to Korean Application No. 10-2020-0054196, filed on May 7, 2020 in the Korean Intellectual Property Office, the contents of which are all hereby incorporated by reference herein in their entirety.

BACKGROUND OF THE DISCLOSURE

Technical Field

The present invention relates to an interspinous insert, and more particularly, to an interspinous insert used for a spinal operation using an endoscope.

Background Art

To solve the instability of spinal segments after discectomy or posterior decompression, interspinous spacer implantation is performed by inserting an interspinous spacer between a patient's spinous processes.

The interspinous spacer implantation includes processes of incising a predetermined section of a surgical site, inserting a spacer between adjacent spinous processes through the incised portion, surrounding the spinous processes with a strap or band, and fixing the spacer between the spinous processes.

Recently, even in the case of the interspinous spacer implantation, methods are being studied to form several incision holes at a periphery of a surgical site, insert an endoscope and surgical tools through the incision holes, and fix an interspinous spacer without incising a predetermined section of a surgical site.

However, because a size of the interspinous spacer in the related art is larger than a size of the incision hole, there is a problem in that the interspinous spacer cannot pass through the incision hole.

RELATED PATENT DOCUMENT (Patent Document 1) Korean Patent No. 10-1661635

SUMMARY OF THE DISCLOSURE

The present invention has been made in an effort to solve the above-mentioned problem, and an object of the present invention is to provide an endoscopic interspinous insert capable of being inserted into a body through an incision hole during a spinal endoscopic operation.

Technical problems of the present invention are not limited to the aforementioned technical problems, and other technical problems, which are not mentioned above, may be clearly understood by those skilled in the art from the following descriptions.

To achieve the above-mentioned object, an endoscopic interspinous insert according to an embodiment of the present invention may be configured to be inserted between adjacent spinous processes and include: a first support member including a first support body configured to support any one of the adjacent spinous processes, and a plurality of first support protrusions protruding from two opposite ends of the first support body; a second support member including a second support body configured to support the other of the adjacent spinous processes, and a plurality of second support protrusions protruding from two opposite ends of the second support body; and an adjustment member disposed between the first support member and the second support member and configured to adjust a distance between the first support member and the second support member.

The first support member may be disposed at a first position at which the first support member overlaps the second support member or a second position at which the first support member is separated from the second support member and spaced apart from the second support member at a predetermined distance.

The adjustment member may be integrated with at least one of the first support member and the second support member.

The first support member may include a first frame having a first accommodation portion configured to accommodate one end of the adjustment member, and the second support member may include a second frame having a second accommodation portion configured to accommodate the other end of the adjustment member.

The adjustment member may include: a cylindrical adjustment body; and a plurality of adjustment side teeth protruding from an outer peripheral surface of the adjustment body, and the first and second frames may include a plurality of frame side teeth configured to engage with the plurality of adjustment side teeth.

The plurality of adjustment side teeth may each include first and second inclined surfaces having different inclination angles.

The adjustment member may include a compression spring.

The endoscopic interspinous insert may further include: a locking member configured to fix the first support member to the second support member to prevent the first support member from being separated from the second support member.

The locking member may include: a hook coupled to the first support member; and a catching portion coupled to the second support member and configured such that a part of the hook is inserted into the catching portion.

The adjustment member may be rotatably disposed between the first support member and the second support member.

The endoscopic interspinous insert may further include: a locking member configured to maintain a distance between the first support member and the second support member and restrict movements of the first and second support members, in which the locking member includes: a first locking block inserted into the adjustment member; a second locking block inserted between the first support member and the second support member; a connection flange configured to connect the first locking block and the second locking block; and a fixing screw configured to be fixed to the adjustment member while penetrating the first locking block and the second locking block.

The adjustment member may include: a screw bevel gear rotatably disposed in the second support member and coupled to the first support member; and an adjustment bevel gear configured to transmit power to the screw bevel gear.

The first support member may include a first adjustment groove, the second support member may include a second adjustment groove, and the adjustment member may be screw-coupled to the first adjustment groove and the second adjustment groove.

The endoscopic interspinous insert may further include: a locking member configured to maintain a distance between the first support member and the second support member and restrict movements of the first and second support members.

According to the embodiment of the present invention, the endoscopic interspinous insert may be inserted into the body through the incision hole and then deformed in the body to have a shape suitable for a surgical operation, which makes it possible to perform the surgical operation through the incision hole without incising a predetermined section of a surgical site.

DETAILED DESCRIPTION OF THE EMBODIMENT

Figure 1A:
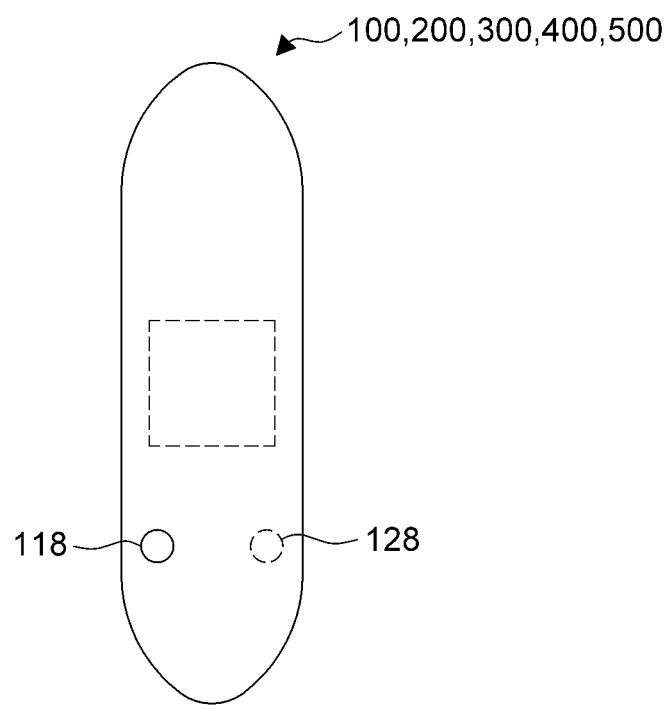
FIGS. 1A and 1B are views illustrating a process of spreading an endoscopic interspinous insert according to an embodiment of the present invention.

Hereinafter, various exemplary embodiments will be described in more detail with reference to the accompanying drawings. The exemplary embodiments disclosed in the present specification may be variously modified. Specific embodiments will be illustrated in the drawings and described in detail in the detailed description. However, the specific embodiments illustrated in the accompanying drawings are merely intended to facilitate understanding of various embodiments. Therefore, the technical spirit is not limited by the specific embodiments illustrated in the accompanying drawings, and the scope of the present invention should be understood as including all equivalents or substitutes included in the spirit and technical scope of the present invention.

The terms including ordinal numbers such as 'first,' 'second,' and the like may be used to describe various constituent elements, but the constituent elements are not limited by the terms. These terms are used only to distinguish one constituent element from another constituent element.

In the present specification, it should be understood the terms "comprises," "comprising," "includes," "including," "containing," "has," "having" or other variations thereof are inclusive and therefore specify the presence of stated features, integers, steps, operations, elements, components, or combinations thereof, but do not preclude the presence or addition of one or more other features, integers, steps, operations, elements, components, or combinations thereof. When one constituent element is described as being "coupled" or "connected" to another constituent element, it should be understood that one constituent element can be coupled or connected directly to another constituent element, and an intervening constituent element can also be present between the constituent elements. When one constituent element is described as being "coupled directly to" or "connected directly to" another constituent element, it should be understood that no intervening constituent element is present between the constituent elements.

Meanwhile, the term "module" or "unit" used for a constituent element used in the present specification performs at least one function or operation. Further, the "module" or "unit" may perform the function or operation by hardware, software, or a combination of hardware and software. In addition, except for the "module" or "unit" that should be performed in specific hardware or performed by at least one processor, a plurality of "modules" or a plurality of "units" may be integrated into at least one module. Singular expressions include plural expressions unless clearly described as different meanings in the context.

In addition, in the description of the present invention, the specific descriptions of related well-known functions or configurations will be summarized or omitted when it is determined that the specific descriptions may unnecessarily obscure the subject matter of the present invention.

Figure 1B:
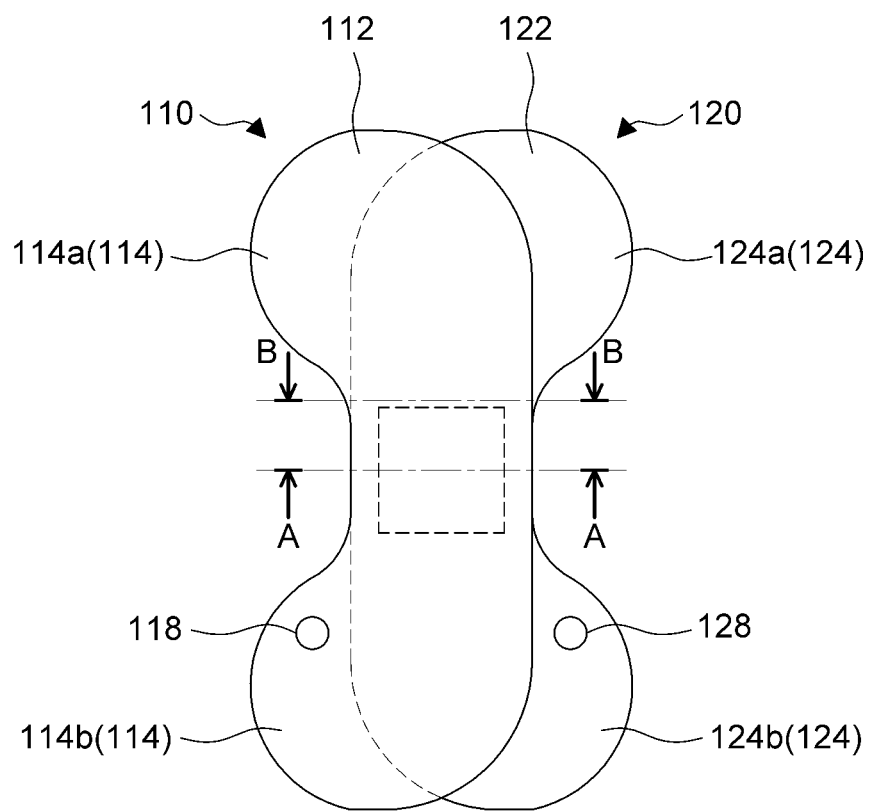
Figure 1C:
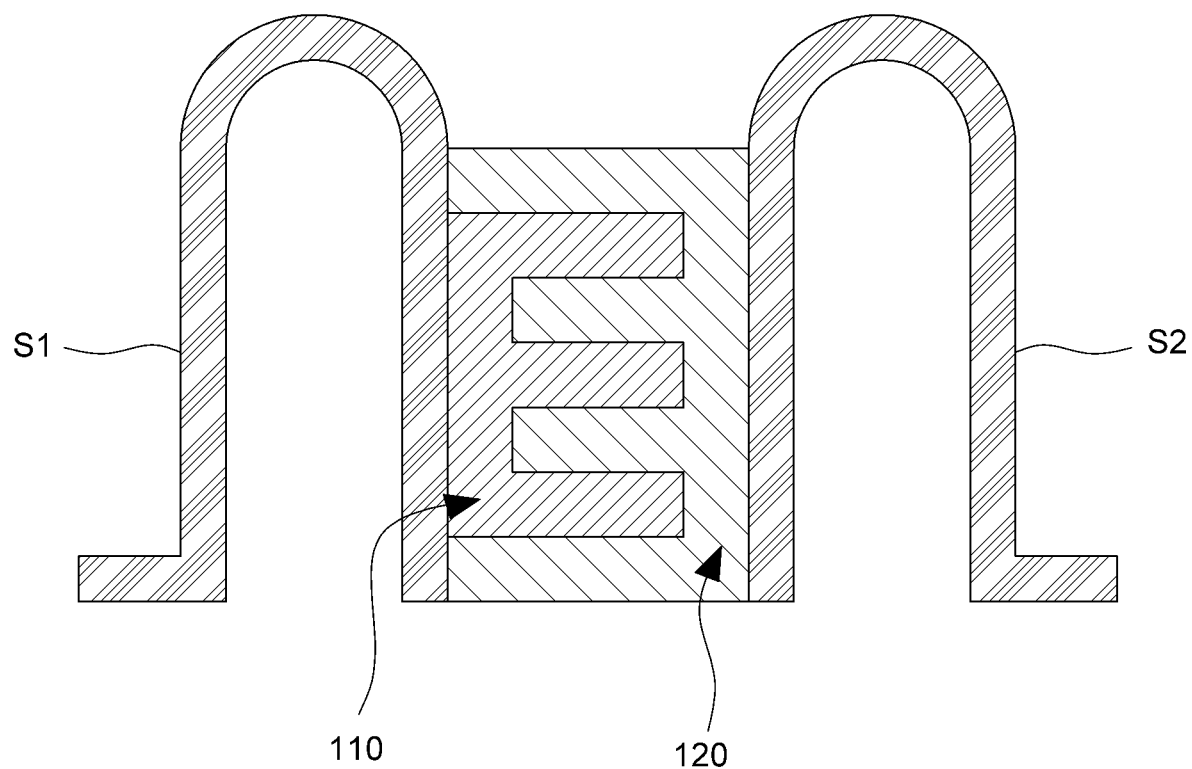
FIG. 1C is a cross-sectional view taken along line B-B in FIG. 1B.
Figure 1D:
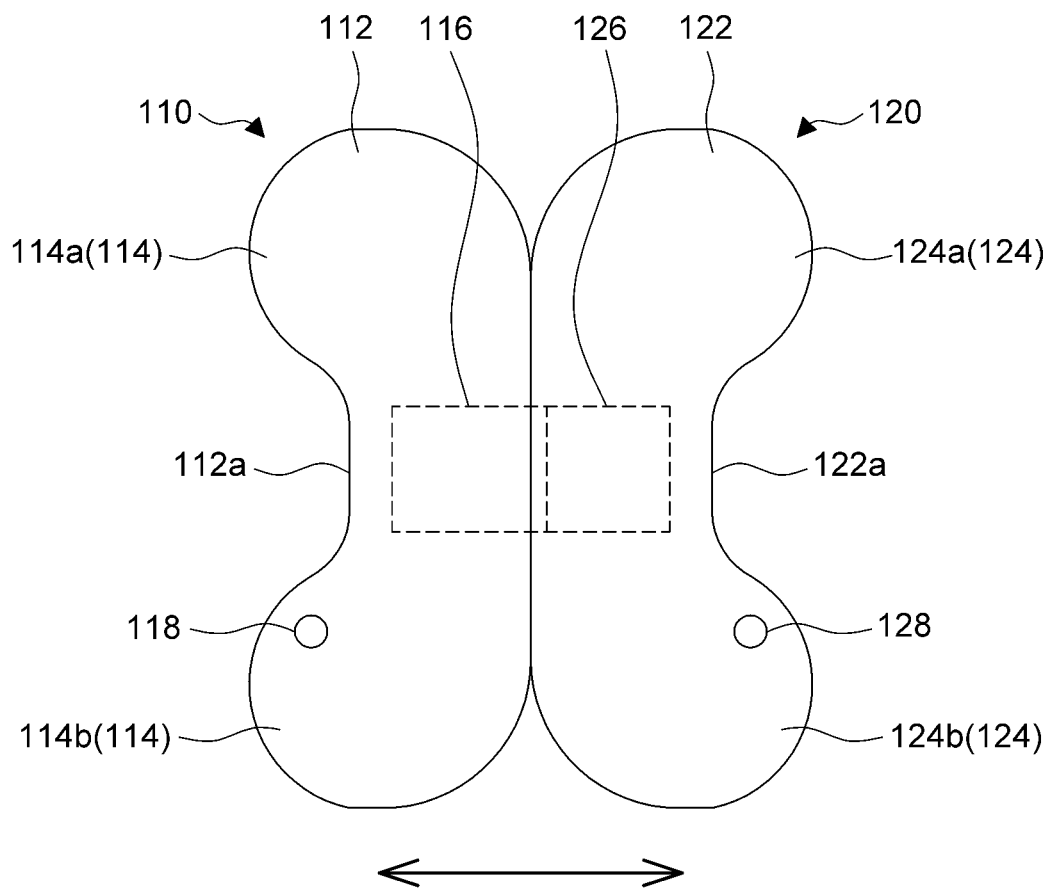
FIG. 1D is a view illustrating a process of spreading the endoscopic interspinous insert according to the embodiment of the present invention.

FIGS. 1A and 1B are views illustrating a process of spreading an endoscopic interspinous insert according to an embodiment of the present invention. FIG. 1C is a cross-sectional view taken along line B-B in FIG. 1B, and FIG. 1D is a view illustrating a process of spreading the endoscopic interspinous insert according to the embodiment of the present invention. To help understand the present invention, FIG. 1C additionally illustrates cross-sections of spinous processes between which the interspinous insert is inserted.

Figure 2A:
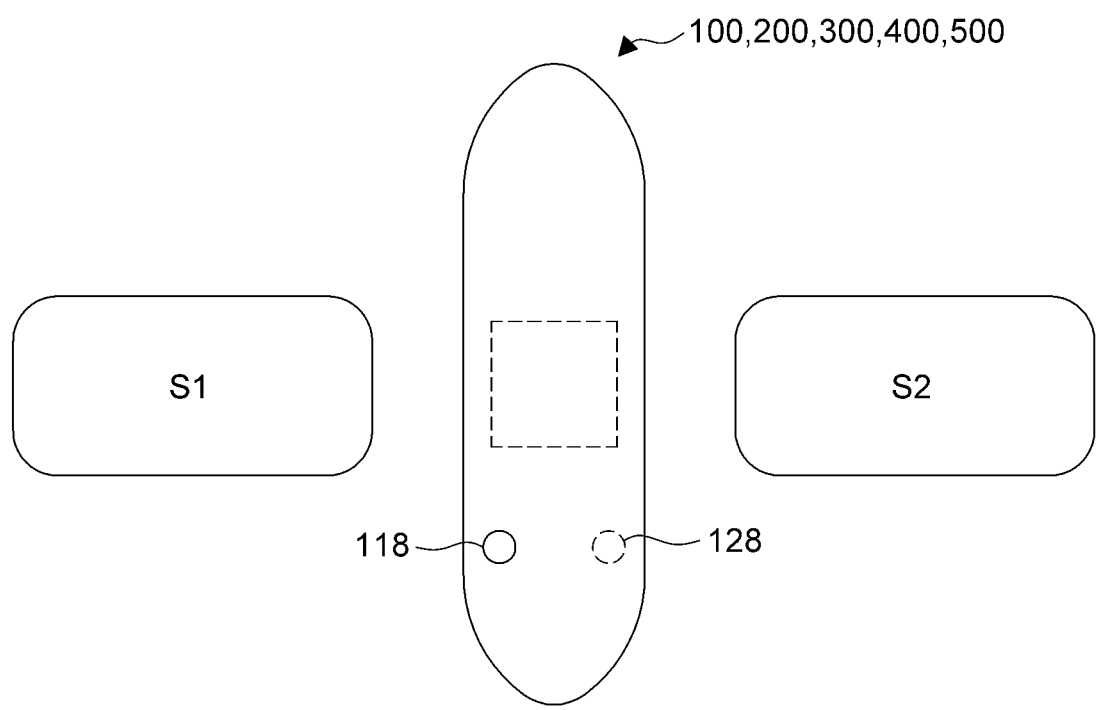
FIGS. 2A, 2B, and 2C are views illustrating a process of disposing the endoscopic interspinous insert according to the embodiment of the present invention between spinous processes.
Figure 2B:
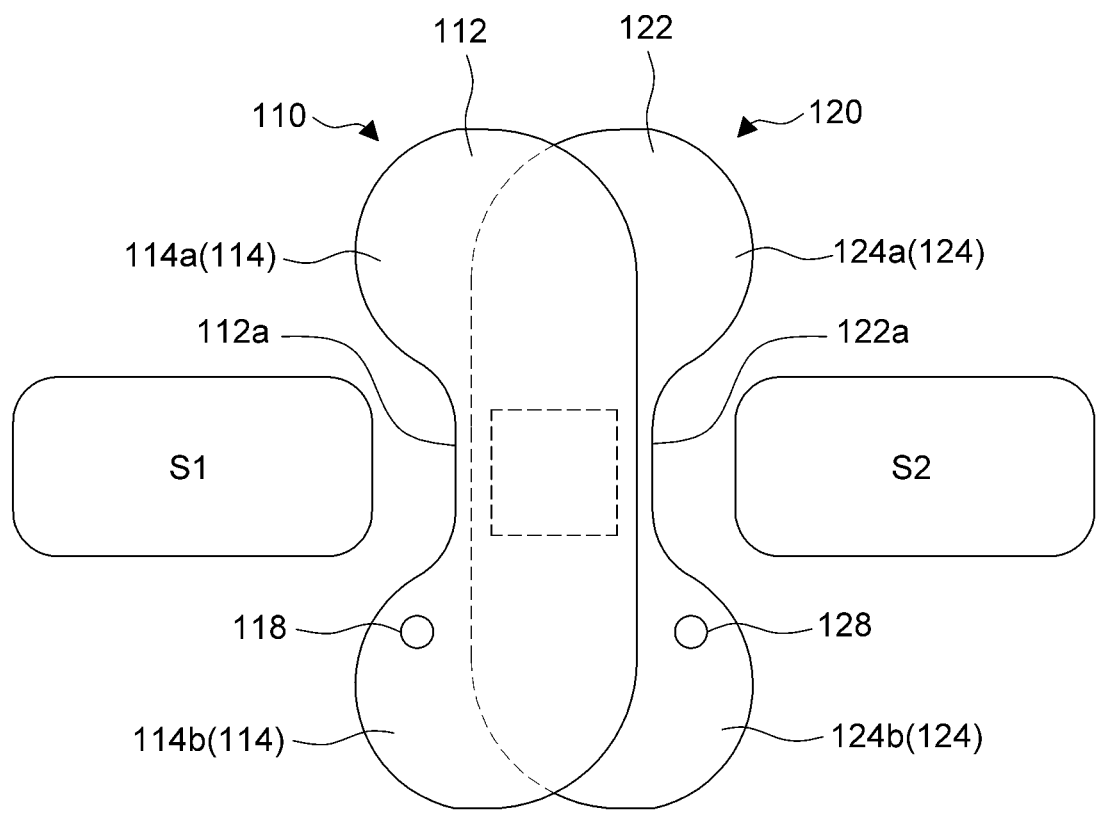
Figure 2C:
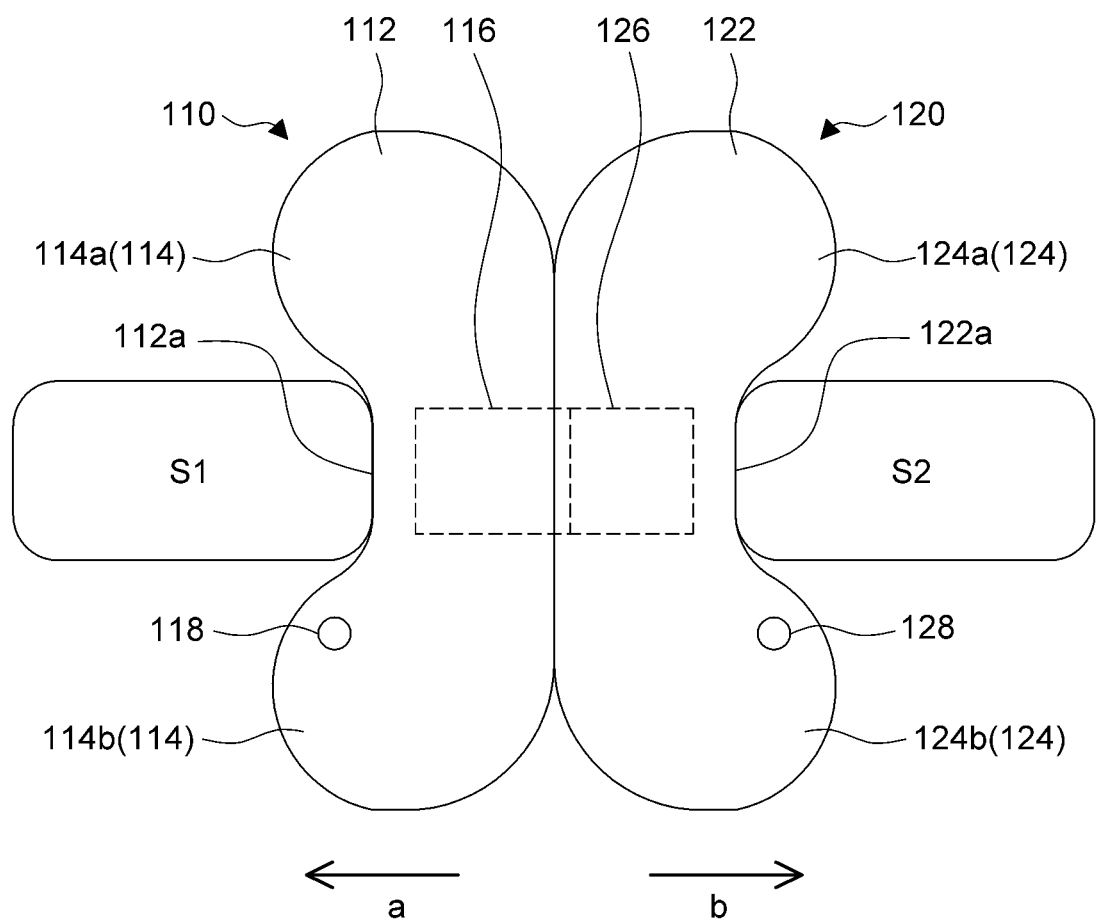

FIGS. 2A, 2B, and 2C are views illustrating a process of disposing the endoscopic interspinous insert according to the embodiment of the present invention between spinous processes.

Figure 3A:
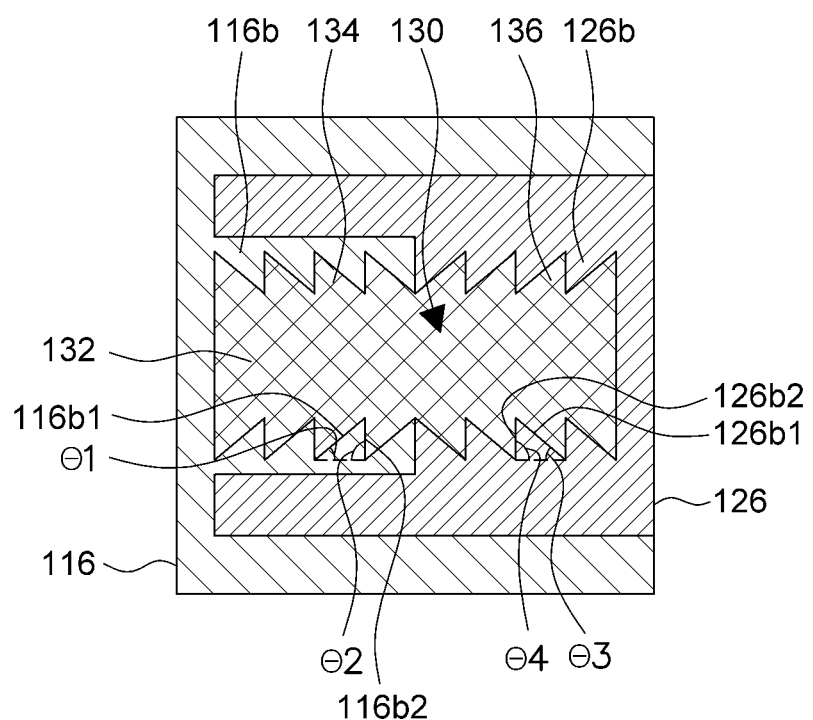
FIG. 3A is a cross-sectional view taken along line A-A in FIG. 1B.
Figure 3B:
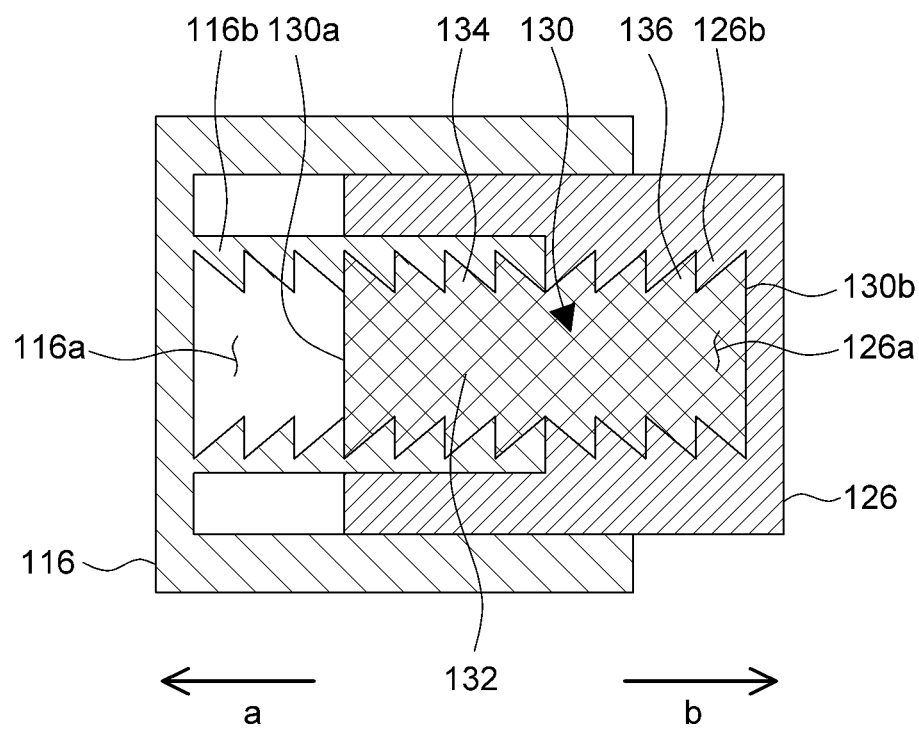
FIG. 3B is a view illustrating a process of adjusting a distance between a first frame and a second frame.

FIG. 3A is a cross-sectional view taken along line A-A in FIG. 1B, and FIG. 3B is a view illustrating a process of adjusting a distance between a first frame and a second frame.

Referring to FIGS. 1A to 3B, an endoscopic interspinous insert 100 according to the embodiment of the present invention includes a first support member 110, a second support member 120, and an adjustment member 130.

The first support member 110 is configured to come into contact with at least a part of an outer surface of any one S1 of adjacent spinous processes. The first support member 110 includes a first support body 112, a plurality of first support protrusions 114, a first frame 116, and a first insertion groove 118.

The first support body 112 may support any one S1 of the spinous processes in a state in which the endoscopic interspinous insert 100 is inserted between the adjacent spinous processes S1 and S2. The first support body 112 may be made of rubber or silicone. In addition, the first support body 112 may be made of various materials having an elastic force.

The first support body 112 may include a first contact surface 112a configured to come into contact with at least a part of the outer surface of any one S1 of the spinous processes.

The first contact surface 112a may have a shape corresponding to at least a part of the outer surface of any one S1 of the spinous processes. The first contact surface 112a may have a mesh structure having relatively higher surface roughness than the other parts of the first support body 112.

Because the first contact surface 112a has the mesh structure, a frictional force, which occurs when the first contact surface 112a comes into contact with the spinous process S1, may prevent the first contact surface 112a from slipping from the surface of the spinous process S1, such that the interspinous insert 100 may be stably fixed while being disposed between the spinous processes S1 and S2.

The plurality of first support protrusions 114 protrudes from two opposite ends of the first support body 112. Any one 114a of the plurality of first support protrusions 114 may extend from one end of the first contact surface 112a, and the other 114b of the plurality of first support protrusions 114 may extend from the other end of the first contact surface 112a. The plurality of first support protrusions 114 may each have a rounded shape to surround the outer surface of any one S1 of the spinous processes. In the state in which the interspinous insert 100 is disposed between the spinous processes S1 and S2, any one S1 of the spinous processes is disposed between the plurality of first support protrusions 114 in a state in which the outer surface of any one S1 of the spinous processes is surrounded by the plurality of first support protrusions 114. Therefore, the first support member 110 may be prevented from separating from any one S1 of the spinous processes.

The first frame 116 may be coupled to an inner portion of the first support body 112. The first frame 116 may have a hollow cylindrical shape so that the first frame 116 may engage with the adjustment member 130 and accommodate the adjustment member 130.

The first frame 116 may be made of a material that is harmless to a human body and may be disinfected. For example, the first frame 116 may be made of a metallic material such as stainless steel or a plastic material. In addition, the first frame 116 may be made of various materials having rigidity and high corrosion resistance.

The first frame 116 includes a first accommodation portion 116a configured to accommodate one end 130a of the adjustment member 130, and a plurality of first teeth 116b protruding from an inner surface of the first frame 116 toward the first accommodation portion 116a. The plurality of first teeth 116b is arranged in a direction in which the first support member 110 moves.

The first teeth 116b each have a first inclined surface 116b1 configured to define a first inclination angle $\theta 1$ with respect to the horizontal plane, and a second inclined surface 116b2 configured to define a second inclination angle $\theta 2$ with respect to the horizontal plane. The second inclination angle $\theta 2$ has a larger value than the first inclination angle $\theta 1$.

The first insertion groove 118 has a shape concave from an outer surface of the first support body 112 toward an inner side of the first support body 112 so that a medical surgical instrument (not illustrated) such as Kelly forceps may be inserted and fixed into the first support body 112. The first insertion groove 118 may have a circular shape, an elliptical shape, or a polygonal shape so that various tools such as medical forceps, pincers, medical drivers, or wrenches may be inserted into the first insertion groove 118.

The second support member 120 is configured to come into contact with at least a part of an outer surface of the other S2 of the adjacent spinous processes. As illustrated in FIG. 1C, the second support member 120 may be configured to overlap the first support member 110. The overlapping structure may serve as a guide that enables the support members 110 and 120 to move horizontally while moving away from each other and prevent rotational separation in which two opposite wings are twisted.

The second support member 120 includes a second support body 122, a plurality of second support protrusions 124, a second frame 126, and a second insertion groove 128.

The second support body 122 may support the other S2 of the spinous processes in a state in which the endoscopic interspinous insert 100 is inserted between the adjacent spinous processes S1 and S2. The second support body 122 may be made of rubber or silicone. In addition, the second support body 122 may be made of various materials having an elastic force.

The second support body 122 may include a second contact surface 122a configured to come into contact with at least a part of the outer surface of the other S2 of the spinous processes.

The second contact surface 122a may have a shape corresponding to at least a part of the outer surface of the other S2 of the spinous processes. The second contact surface 122a may have a mesh structure having relatively higher surface roughness than the other parts of the second support body 122.

Because the second contact surface 122a has the mesh structure, a frictional force, which occurs when the second contact surface 122a comes into contact with the spinous process S2, may prevent the second contact surface 122a from slipping from the surface of the spinous process S2, such that the interspinous insert 100 may be stably fixed while being disposed between the spinous processes S1 and S2.

The plurality of second support protrusions 124 protrudes from two opposite ends of the second support body 122. Any one 124*a* of the plurality of second support protrusions 124 may extend from one end of the second contact surface 122*a*, and the other 124*b* of the plurality of second support protrusions 124 may extend from the other end of the second contact surface 122*a*.

Because the plurality of first support protrusions 114 and the plurality of second support protrusions 124 are made of elastic materials such as sponge, rubber, or silicone, the interspinous insert 100 may be deformed in a streamlined shape, e.g., a shape of a bullet when the interspinous insert 100 is held by a medical surgical instrument (not illustrated) and the plurality of first support protrusions 114 and the plurality of second support protrusions 124 are pressed.

Therefore, the interspinous insert 100 may pass through an incision hole (not illustrated) in a state in which the interspinous insert 100 is held by a medical surgical instrument (not illustrated) such as Kelly forceps and deformed in a streamlined shape as illustrated in FIG. 1A.

The plurality of second support protrusions 124 may each have a rounded shape to surround the outer surface of the other S2 of the spinous processes. In the state in which the interspinous insert 100 is disposed between the spinous processes S1 and S2, the other S2 of the spinous processes is disposed between the plurality of second support protrusions 124 in a state in which the outer surface of the other S1 of the spinous processes is surrounded by the plurality of second support protrusions 124. Therefore, the second support member 120 may be prevented from separating from the other S2 of the spinous processes.

The second frame 126 may be coupled to the second support body 122. The second frame 126 may have a hollow cylindrical shape so that the second frame 126 may engage with the adjustment member 130 and accommodate the adjustment member 130.

The second frame 126 may be made of a material that is harmless to a human body and may be disinfected. For example, the second frame 126 may be made of a metallic material such as stainless steel or a plastic material. In addition, the second frame 126 may be made of various materials having rigidity and high corrosion resistance.

The second frame 126 includes a second accommodation portion 126*a* configured to accommodate the other end 130*b* of the adjustment member 130, and a plurality of second teeth 126*b* protruding from an inner surface of the second frame 126 toward the second accommodation portion 126*a*. The plurality of second teeth 126*b* is arranged in a direction in which the second support member 120 moves.

The second teeth 126*b* each have a third inclined surface 126*b*1 configured to define a third inclination angle $\theta 3$ with respect to the horizontal plane, and a fourth inclined surface 126*b*2 configured to define a fourth inclination angle $\theta 4$ with respect to the horizontal plane. The fourth inclination angle $\theta 4$ has a larger value than the third inclination angle $\theta 3$. The third inclination angle $\theta 3$ may be equal to the first inclination angle $\theta$, and the fourth inclination angle $\theta 4$ may be equal to the second inclination angle $\theta 2$.

The plurality of first teeth 116*b* and the plurality of second teeth 126*b* collectively constitute frame side teeth.

The second insertion groove 128 has a shape concave from an outer surface of the second support body 122 toward an inner side of the second support body 122 so that a medical surgical instrument may be inserted and fixed into the second support body 122. The second insertion groove 128 may have a circular shape, an elliptical shape, or a polygonal shape so that various tools such as medical scissors, pincers, medical drivers, or wrenches may be inserted into the second insertion groove 128.

The adjustment member 130 is disposed between the first support member 110 and the second support member 120. The adjustment member 130 is configured to adjust a distance between the first frame 116 and the second frame 126.

The adjustment member 130 includes a cylindrical adjustment body 132, and a plurality of third teeth 134 and a plurality of fourth teeth 136 protruding from an outer peripheral surface of the adjustment body 132. The plurality of third teeth 134 and the plurality of fourth teeth 136 collectively constitute adjustment side teeth. The adjustment member may be made of a material such as silicone, rubber, plastic material, or other synthetic metallic materials having elasticity and strength.

The plurality of third teeth 134 respectively engages with the plurality of first teeth 116*b*, and the plurality of fourth teeth 136 respectively engages with the plurality of second teeth 126*b*.

As described above, the first teeth 116*b* each have the first inclined surface 116*b*1 configured to define the first inclination angle $\theta$ with respect to the horizontal plane, and the second inclined surface 116*b*2 configured to define the second inclination angle $\theta$ with respect to the horizontal plane, and the second inclination angle $\theta 2$ has a larger value than the first inclination angle $\theta 1$. Therefore, in the state in which the plurality of third teeth 134 respectively engages with the plurality of first teeth 116*b*, the plurality of third teeth 134 may each move along the first inclined surface 116*b*1 having a relatively gradual inclination angle, but a movement of each of the plurality of third teeth 134 along the second inclined surface 116*b*2 having a relatively steep inclination angle is restricted.

Likewise, the second teeth 126*b* each have the third inclined surface 126*b*1 configured to define the third inclination angle $\theta 3$ with respect to the horizontal plane, and the fourth inclined surface 116*b*2 configured to define the fourth inclination angle $\theta 4$ with respect to the horizontal plane, and the fourth inclination angle $\theta 4$ has a large value than the third inclination angle $\theta 3$. Therefore, in the state in which the plurality of fourth teeth 136 respectively engages with the plurality of second teeth 126*b*, the plurality of fourth teeth 136 may each move along the third inclined surface 126*b*1 having a relatively gradual inclination angle, but a movement of each of the plurality of fourth teeth 136 along the fourth inclined surface 126*b*2 having a relatively steep inclination angle is restricted.

As illustrated in FIGS. 3A and 3B, a fastening structure between the adjustment member 130 and the first frame 116 and a fastening structure between the adjustment member 130 and the second frame 126 allow the first support member 110 to move only in a first direction a and allow the second support member 120 to move only in a second direction b opposite to the first direction a. That is, the first support member 110 and the second support member 120 only move in the direction in which the first support member 110 and the second support member 120 move away from each other.

Hereinafter, a process of inserting and fixing the interspinous insert 100 between the spinous processes S1 and S2 will be described.

Referring to FIG. 2A, the interspinous insert 100 may pass through the incision hole (not illustrated) and be disposed between the spinous processes S1 and S2 in the state in which the interspinous insert 100 is held by the medical surgical instrument (not illustrated) and deformed in a streamlined shape. In this case, the first support member 110 and the second support member 120 of the interspinous insert 100 may overlap each other. A tool, such as medical forceps or pincers, capable of adjusting and decreasing a distance between two opposite ends thereof, may be used as the medical surgical instrument.

Referring to FIGS. 2B, 2C, 3A, and 3B, when the interspinous insert 100 is released in the state in which the interspinous insert 100 is inserted between the spinous processes S1 and S2, the plurality of first support protrusions 114 and the plurality of second support protrusions 124 protrude by the elastic force. Specifically, the plurality of first support protrusions 114 may protrude in the first direction a, and the plurality of second support protrusions 124 may protrude in the second direction b.

Next, two opposite ends of a surgical tool (not illustrated) such as forceps are respectively inserted into the first insertion groove 118 and the second insertion groove 128, and the two opposite ends of the surgical tool (not illustrated) inserted into the first insertion groove 118 and the second insertion groove 128 are moved away from each other. Therefore, the first support member 110 moves in the first direction a, and the second support member 120 moves in the second direction b, such that a distance between the first support member 110 and the second support member 120 increases. In this case, as described above, the fastening structure between the adjustment member 130 and the first frame 116 and the fastening structure between the adjustment member 130 and the second frame 126 restrict the movement of the first support member 110 in the second direction b and restrict the movement of the second support member 120 in the first direction a.

When the first support member 110 and the second support member 120 are spaced apart from each other at a preset distance, the medical surgical instrument (not illustrated) may be separated from the first insertion groove 118 and the second insertion groove 128. In this state, the first support member 110 and the second support member 120 may be respectively in contact with the spinous processes S1 and S2.

Although not illustrated, when the spinous processes S1 and S2 are tensely surrounded by a strap (not illustrated) in the state in which the interspinous insert 100 is inserted between the spinous processes S1 and S2, the interspinous insert 100 is securely fixed between the spinous processes S1 and S2, and the interspinous insert 100 is prevented from separating from the spinous processes. In addition, the stability of the corresponding spinal segment including the spinous processes S1 and S2 is significantly improved.

The structure in which the first support member 110 and the second support member 120 are provided independently of the adjustment member 130 and coupled to the adjustment member 130 has been described above as an example. However, it is possible to adopt a structure in which the adjustment member 130 may be fixed to or integrated with any one of the first and second support members 110 and 120, and only the other of the first and second support members 110 and 120 may move relative to the adjustment member 130.

In addition, the structure in which the adjustment member 130 has a cylindrical shape has been described as an example, but the present invention is not limited thereto. The shape of the adjustment member 130 and the hollow shapes of the frames may each be a polyhedral shape having a triangular or quadrangular cross-section. In this case, it is possible to adopt a structure in which the teeth configured to engage with the first frame 116 and the second frame 126 may be provided only one surface of the polyhedral shape.

In addition, the present invention is not limited to the configuration in which the endoscopic interspinous insert 100 is inserted between the spinous processes of the vertebra. It is possible to adopt a structure in which the endoscopic interspinous insert 100 is inserted between bones existing in the body or between protrusions of other tissue.

Hereinafter, an endoscopic interspinous insert 200 according to another embodiment of the present invention will be described. A description of parts identical to the above-mentioned parts of the endoscopic interspinous insert 100 according to the embodiment of the present invention will be omitted, and only parts different from the above-mentioned parts of the endoscopic interspinous insert 100 will be described.

Figure 4A:
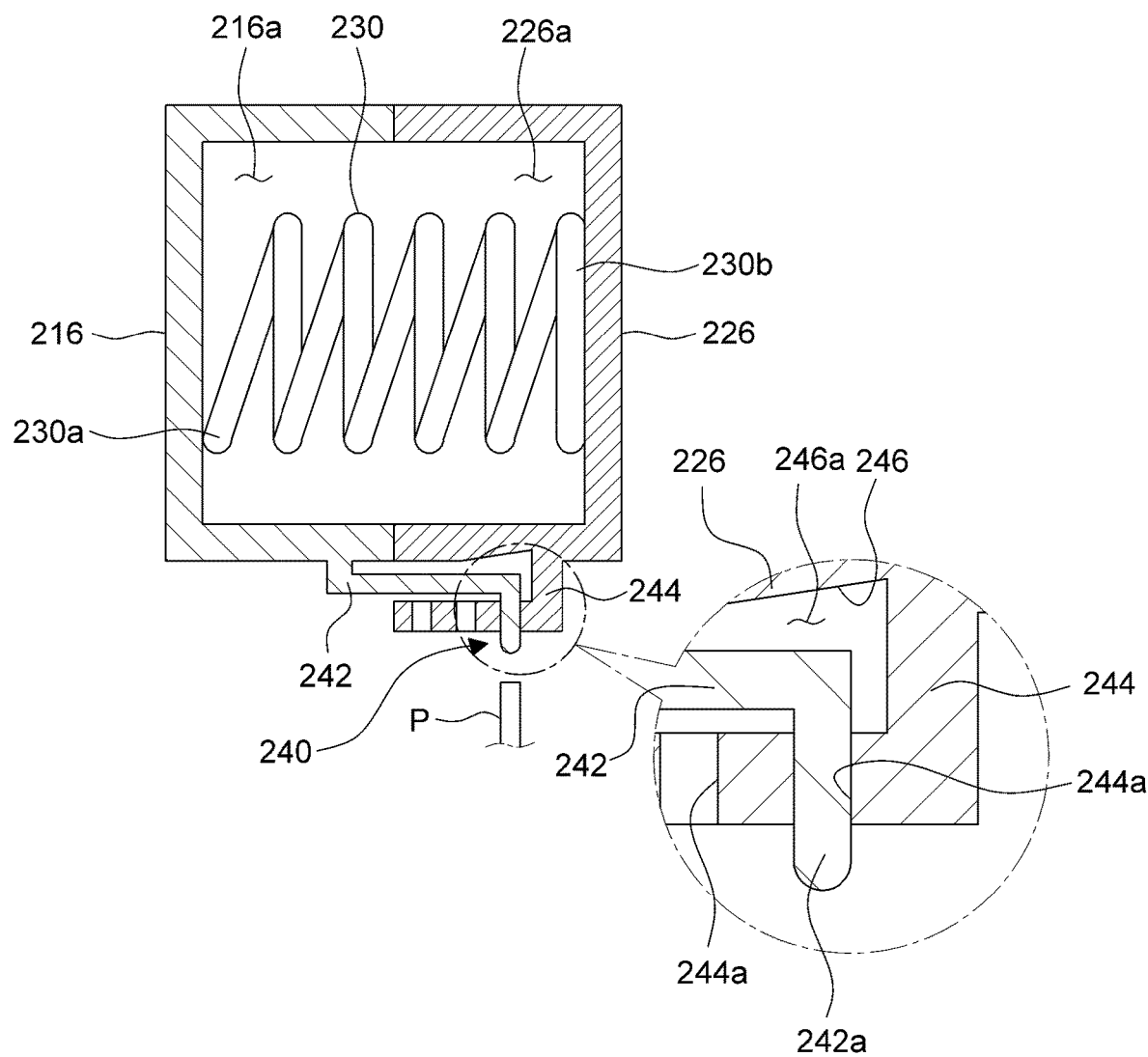
FIG. 4A is a cross-sectional view of a first frame, a second frame, and an adjustment member of an endoscopic interspinous insert according to another embodiment of the present invention.
Figure 4B:
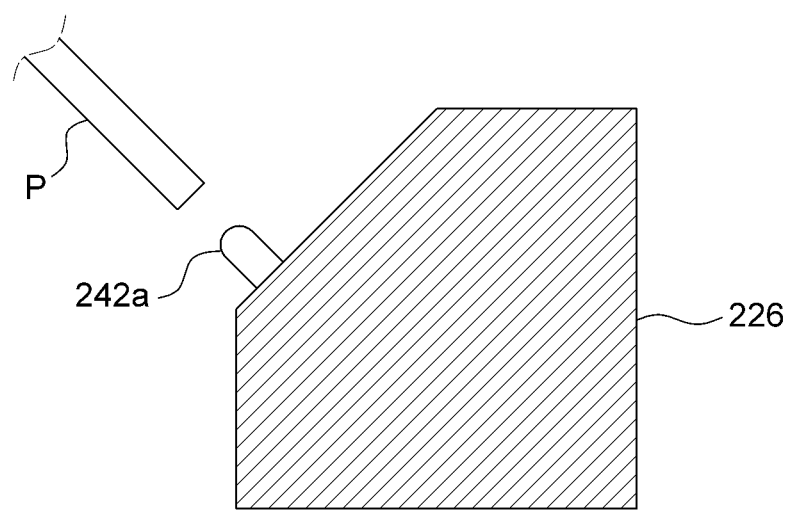
FIG. 4B is a side view of the second frame and the adjustment member of the endoscopic interspinous insert according to the embodiment of the present invention.
Figure 4C:
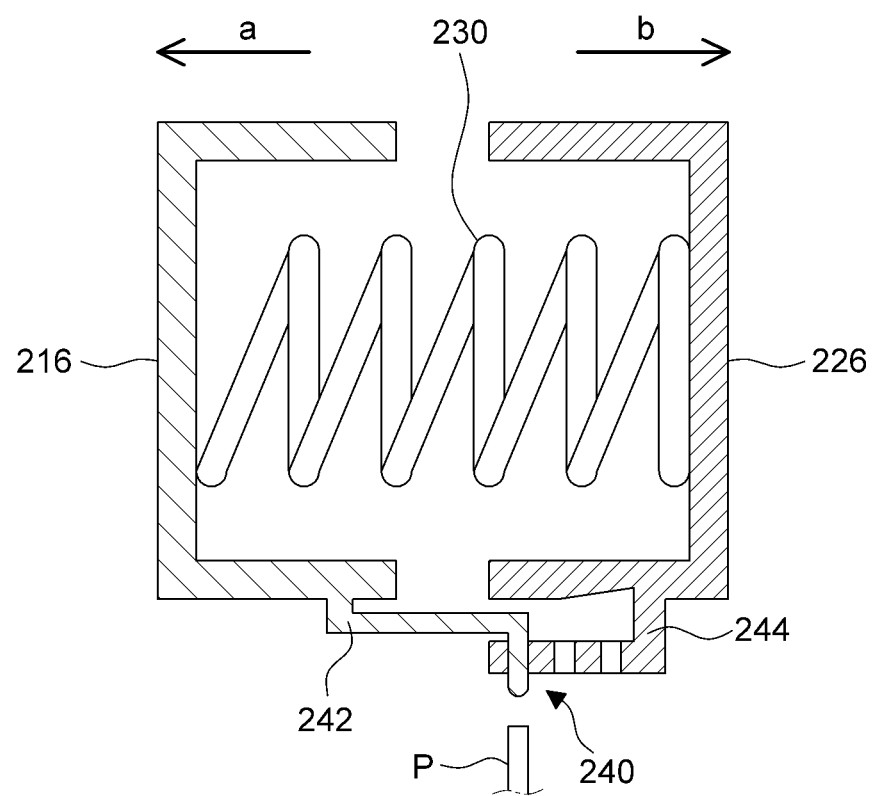
FIG. 4C is a view illustrating a process of adjusting a distance between the first frame and the second frame.

FIG. 4A is a cross-sectional view of a first frame, a second frame, and an adjustment member of an endoscopic interspinous insert according to another embodiment of the present invention, and FIG. 4B is a side view of the second frame and the adjustment member of the endoscopic interspinous insert according to the embodiment of the present invention. FIG. 4C is a view illustrating a process of adjusting a distance between the first frame and the second frame.

Referring to FIGS. 4A and 4C, a first frame 216 may have a hollow cylindrical shape to accommodate an adjustment member 230.

The first frame 216 includes a first accommodation portion 216a configured to accommodate one end 230a of the adjustment member 230.

The first frame 216 may be made of a material that is harmless to a human body and may be disinfected. For example, the first frame 216 may be made of a metallic material such as stainless steel or a plastic material. In addition, the first frame 216 may be made of various materials having rigidity and high corrosion resistance.

A second frame 226 may have a hollow cylindrical shape to accommodate the adjustment member 230.

The second frame 226 includes a second accommodation portion 226a configured to accommodate the other end 230b of the adjustment member 230.

The second frame 226 may be made of a material that is harmless to a human body and may be disinfected. For example, the second frame 226 may be made of a metallic material such as stainless steel or a plastic material. In addition, the second frame 226 may be made of various materials having rigidity and high corrosion resistance.

The adjustment member 230 is disposed between the first frame 216 and the second frame 226.

The adjustment member 230 may be configured as a cylindrical elastic body. Specifically, the adjustment member 230 may include a compression coil spring that resists against a compressive force. A resistive force of the compression coil spring against an external compressive force is proportional to a spring constant value (unit: N/mm) of the compression coil spring. This means that a distance between the first frame 216 and the second frame 226 may be adjusted depending on the spring constant value of the compression coil spring. Therefore, the distance between the first frame 216 and the second frame 226 may be adjusted by adjusting the spring constant value of the compression coil spring.

One end 230a of the adjustment member 230 is accommodated in the first accommodation portion 216a of the first frame 216, and the other end 230b of the adjustment member 230 is accommodated in the second accommodation portion 226a of the second frame 226.

One end 230a of the adjustment member 230 is coupled and fixed to an inner surface of the first frame 216 in the state in which one end 230a of the adjustment member 230 is accommodated in the first accommodation portion 216a of the first frame 216. The other end 230b of the adjustment member 230 is coupled and fixed to an inner surface of the second frame 226 in the state in which the other end 230b of the adjustment member 230 is accommodated in the second accommodation portion 226a of the second frame 226.

A locking member 240 is configured to prevent the first frame 216 from separating from the second frame 226 and includes a hook 242 coupled to the first frame 216, and a catching portion 244 extending from the second frame 226.

The hook 242 is provided to be tiltable and includes a catching protrusion 242a protruding from one end thereof. The hook 242 mounted on a material having an elastic force that may return the hook 242 to an original shape.

The catching protrusion 242a may be coupled to the catching portion 244 or separated from the catching portion 244 from the state in which the catching protrusion 242a is coupled to the catching portion 244.

The catching portion 244 includes a plurality of catching holes 244a so that the catching protrusion 242a is inserted into and caught by the catching hole 244a. The plurality of catching holes 244a is disposed to be spaced apart from one another in a direction in which the adjustment member 230 is extended or compressed.

When the catching protrusion 242a is inserted into or caught by any one of the catching holes 244a, the hook 242 is fixed to the catching portion 244. When the hook 242 is fixed by being caught by the catching portion 244, the first frame 216 is fixed to the second frame 226.

The locking member 240 may further include an inclined surface 246 concavely formed in the second frame 226. The inclined surface 246 defines an accommodation space 246a between the catching portion 244 and a part of the second frame 226. One end of the hook 242 including the catching protrusion 242a separated from any one of the catching holes 244a is accommodated in the accommodation space 246a. Therefore, one end of the hook 242 does not interfere with the second frame 226.

Hereinafter, a process of adjusting the distance between the first frame 216 and the second frame 226 will be described.

Referring to FIGS. 4A to 4C, when a surgical tool P presses the catching protrusion 242a caught by any one of the plurality of catching holes 244a, the catching protrusion 242a separates from any one of the plurality of catching holes 244a. As illustrated in FIG. 4B, the catching protrusion 242a is disposed to be inclined, and the surgical tool P moves inclinedly and presses the catching protrusion 242a.

One end of the hook 242 including the catching protrusion 242a separated from any one of the plurality of catching holes 244a is accommodated in the accommodation space 246a.

When one end of the hook 242 is separated from any one of the plurality of catching holes 244a and accommodated in the accommodation space 246a, the first frame 216 becomes in an unlocked state in which the first frame 216 may freely move from the second frame 226.

In addition, because the elastic force of the adjustment member 230 presses the first frame 216 in the first direction a and presses the second frame 226 in the second direction b, the first frame 216 moves in the first direction a and the second support member 220 moves in the second direction b at the same time when the first frame 216 is unlocked.

Once the catching protrusion 242a is separated from the plurality of catching holes 244a, the first frame 216 and the second frame 226 are moved away from each other by the elastic force of the adjustment member 230. In this case, the separated catching protrusion 242a may be moved by the elastic force of the adjustment member 230 and caught by another catching hole 244a by the elastic force that returns the catching protrusion 242a to an original shape. In the state in which the first frame 216 is spaced apart from the second frame 226, the first frame 216 is fixed by the catching protrusion 242a caught by another catching hole 244a.

The hook 242 and the catching portion 244 may each be made of a hard material so that the hook 242 and the catching portion 244 are not easily broken. Therefore, it is possible to prevent the hook 242 and the catching portion 244 from being damaged by a patient's motion such as when the patient repeatedly bends his/her waist. Therefore, it is possible to prevent the catching protrusion 242a from separating from the catching hole 244a or prevent the catching protrusion 242a from colliding with the catching portion 244 and being broken.

Hereinafter, an endoscopic interspinous insert 300 according to still another embodiment of the present invention will be described. A description of parts identical to the above-mentioned parts of the endoscopic interspinous insert 100 according to the embodiment of the present invention will be omitted, and only parts different from the above-mentioned parts of the endoscopic interspinous insert 100 will be described.

Figure 5A:
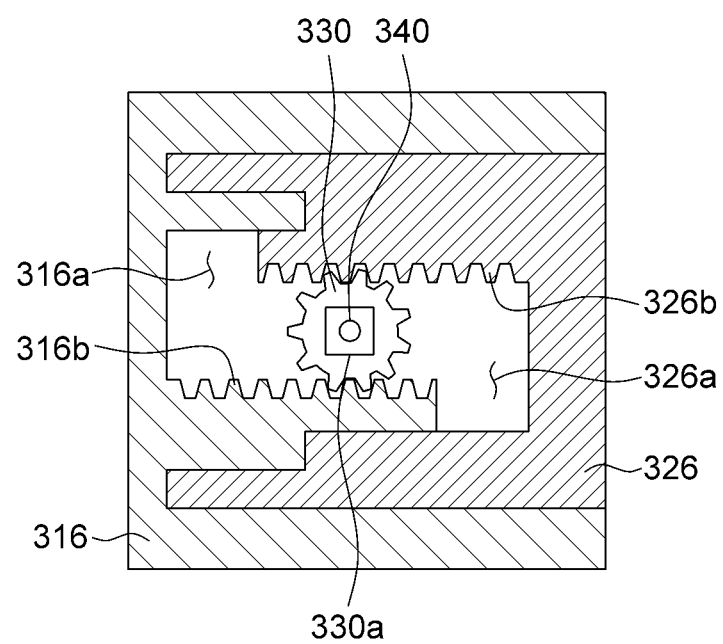
FIG. 5A is a cross-sectional view of a first frame, a second frame, and an adjustment member of an endoscopic interspinous insert according to still another embodiment of the present invention.
Figure 5B:
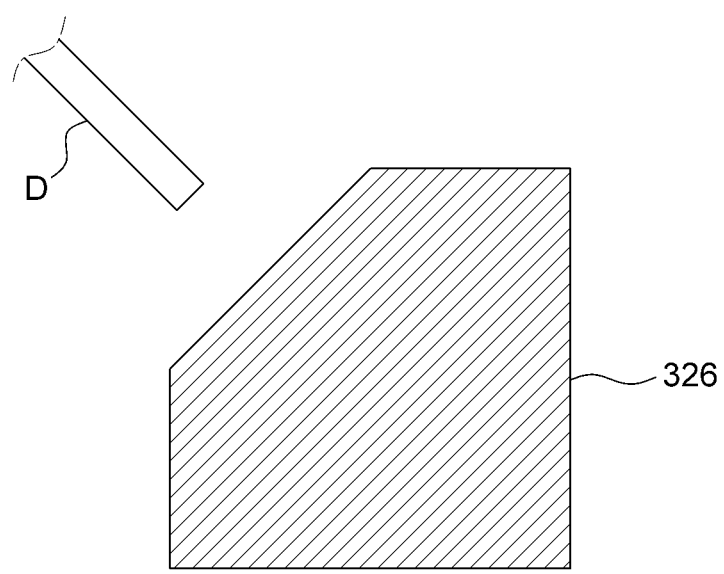
FIG. 5B is a side view of the second frame of the endoscopic interspinous insert according to the embodiment of the present invention.
Figure 5C:
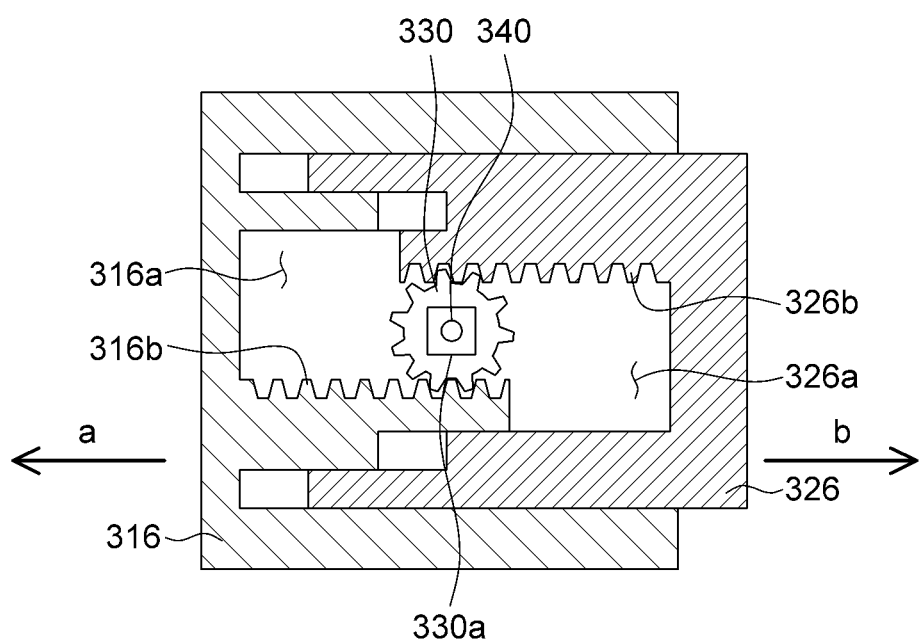
FIG. 5C is a view illustrating a process of adjusting a distance between the first frame and the second frame.
Figure 5D:
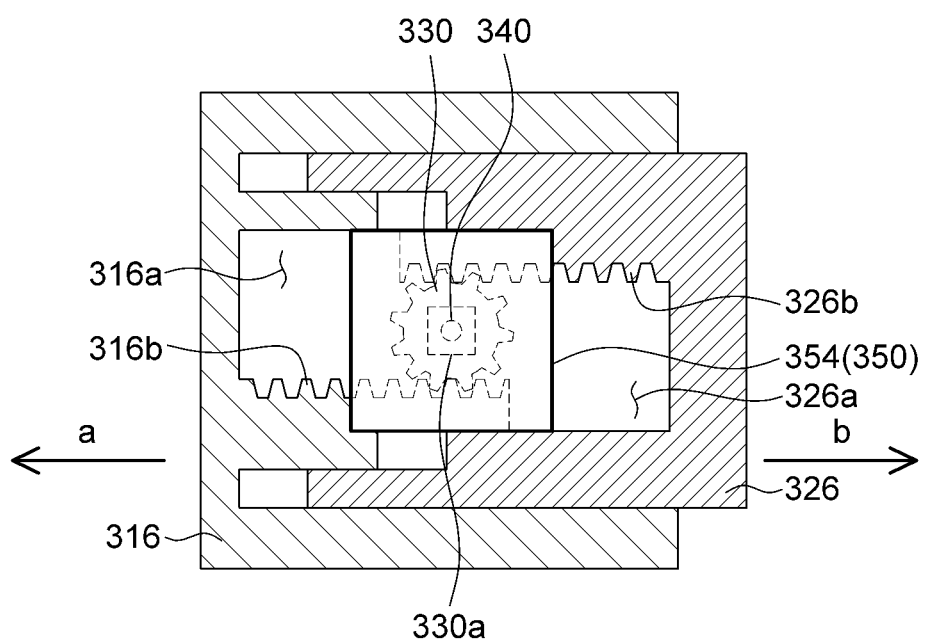
FIG. 5D is a view illustrating a state in which the first frame and the second frame are locked by a locking member.

FIG. 5A is a cross-sectional view of a first frame, a second frame, and an adjustment member of an endoscopic interspinous insert according to still another embodiment of the present invention, and FIG. 5B is a side view of the second frame of the endoscopic interspinous insert according to the embodiment of the present invention. FIG. 5C is a view illustrating a process of adjusting a distance between the first frame and the second frame, and FIG. 5D is a view illustrating a state in which the first frame and the second frame are locked by a locking member.

Referring to FIGS. 5A to 5D, a first frame 316 may have a hollow shape to accommodate a plurality of first teeth 316b that engages with an adjustment member 330.

The first frame 316 may be made of a material that is harmless to a human body and may be disinfected. For example, the first frame 316 may be made of a metallic material such as stainless steel or a plastic material. In addition, the first frame 316 may be made of various materials having rigidity and high corrosion resistance.

The first frame 316 includes a first accommodation portion 316a, and the plurality of first teeth 316b protruding from an inner surface of the first frame 316 toward the first accommodation portion 316a. The plurality of first teeth 316b is arranged in a direction in which the first frame 316 moves.

A second frame 326 may have a hollow shape to accommodate a plurality of second teeth 326b that engages with the adjustment member 330.

The second frame 326 may be made of a material that is harmless to a human body and may be disinfected. For example, the second frame 326 may be made of a metallic material such as stainless steel or a plastic material. In addition, the second frame 326 may be made of various materials having rigidity and high corrosion resistance.

The second frame 326 includes a second accommodation portion 326a, and a plurality of second teeth 326b protruding from an inner surface of the second frame 326 toward the second accommodation portion 326*a*. The plurality of second teeth 326*b* is arranged in a direction in which the second support member 320 moves.

The adjustment member 330 may have a shape of a gear that may engage with the plurality of first teeth 316*b* and the plurality of second teeth 326*b*. The adjustment member 330 may be made of a metallic material such as stainless steel or a plastic material. In addition, the adjustment member 330 may be made of various materials having rigidity and high corrosion resistance.

The adjustment member 330 includes a locking groove 330*a* to which a part of a locking member 350 to be described below is coupled. The locking groove 330*a* is formed concavely from one side of the adjustment member 330 to an inner side of the adjustment member 330 so that a tool D such as a medical driver or a wrench may be inserted into the locking groove 330*a*.

When the tool D such as a medical driver or a wrench is inserted into the locking groove 330*a* and applies torque, a rotational force is transmitted to the adjustment member 330, such that the adjustment member 330 rotates. When the adjustment member 330 rotates, the plurality of first teeth 316*b* and the plurality of second teeth 326*b* engaging with the adjustment member 330 rectilinearly move in opposite directions and move the first frame 316 and the second frame 326.

In the present embodiment, the locking groove 330*a* having a quadrangular shape has been illustrated and described, but the shape of the locking groove 330*a* is not limited to the quadrangular shape. The locking groove 330*a* may have various shapes such as a circular, elliptical, or polygonal shape in addition to the quadrangular shape.

The adjustment member 330 further includes a circular insertion groove 340 into which a fixing screw 358 to be described below may be inserted.

A screw thread (not illustrated) is formed on an inner surface of the insertion groove 340. The fixing screw 358 to be described below may be coupled to the screw thread (not illustrated).

The first frame 316 and the second frame 326 are always moved in the opposite directions by the structure in which the plurality of first teeth 316*b* and the plurality of second teeth 326*b* are respectively disposed at upper and lower sides and engage with the adjustment member 330. That is, the first frame 316 and the second frame 326 may move away from or toward each other depending on a rotation direction of the adjustment member 330.

The adjustment member 330 may be rotatably supported by a rotation support part (not illustrated) coupled to the other end of the adjustment member 330 opposite to one end of the adjustment member 330.

Hereinafter, a process of adjusting a distance between the first frame 316 and the second frame 326 and a process of locking the first frame 316 and the second frame 326 by using the locking member 350 to be described below will be described.

Referring to FIGS. 5A to 5D, when the tool D such as a medical driver or a wrench is inserted into the locking groove 330*a* of the adjustment member 330 and applies torque, the adjustment member 330 rotates, and the plurality of first teeth 316*b* and the plurality of second teeth 326*b* engaging with the adjustment member 330 respectively move in the first direction a and the second direction b, such that the distance between the first frame 316 and the second frame 326 increases. As illustrated in FIG. 5B, the tool D such as a medical driver or a wrench moves inclinedly and is coupled to the adjustment member 330.

In a state in which the first frame 316 and the second frame 326 are sufficiently spaced apart from each other, the locking member 350 is coupled to the first frame 316, the second frame 326, and the locking groove 330*a*, the fixing screw 358 passes through a first through-hole 352*b* of the first locking block 352 and a second through-hole 354*b* of the second locking block 354, and a screw thread 358*c* of the fixing screw 358 is coupled to the screw thread (not illustrated) of the insertion groove 340, such that the movements of the first and second frames 316 and 326 in the first direction a or the second direction b are restricted, and the first frame 316 and the second frame 326 may be locked.

Figure 6A:
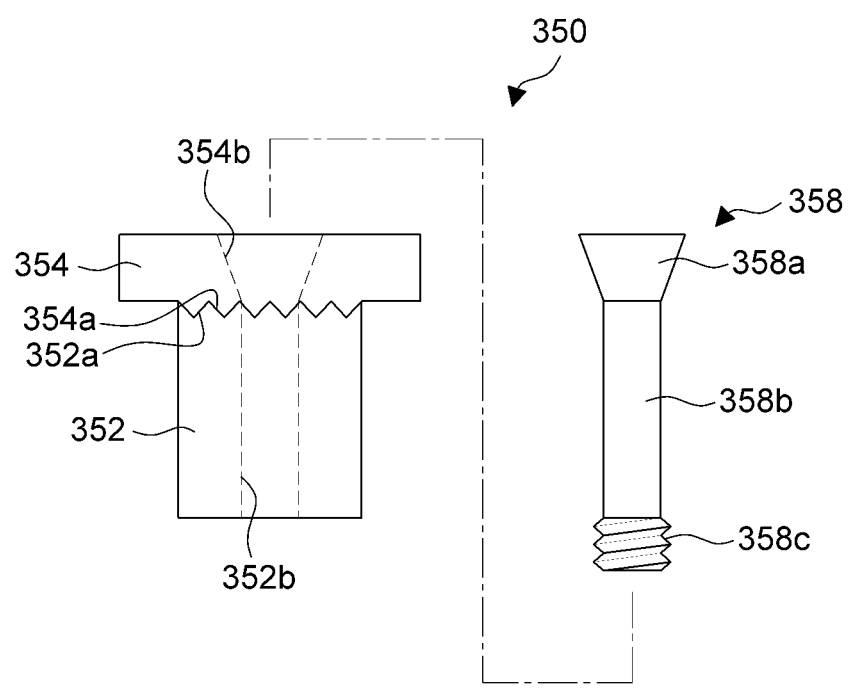
FIG. 6A is a front view illustrating the locking member.
Figure 6B:
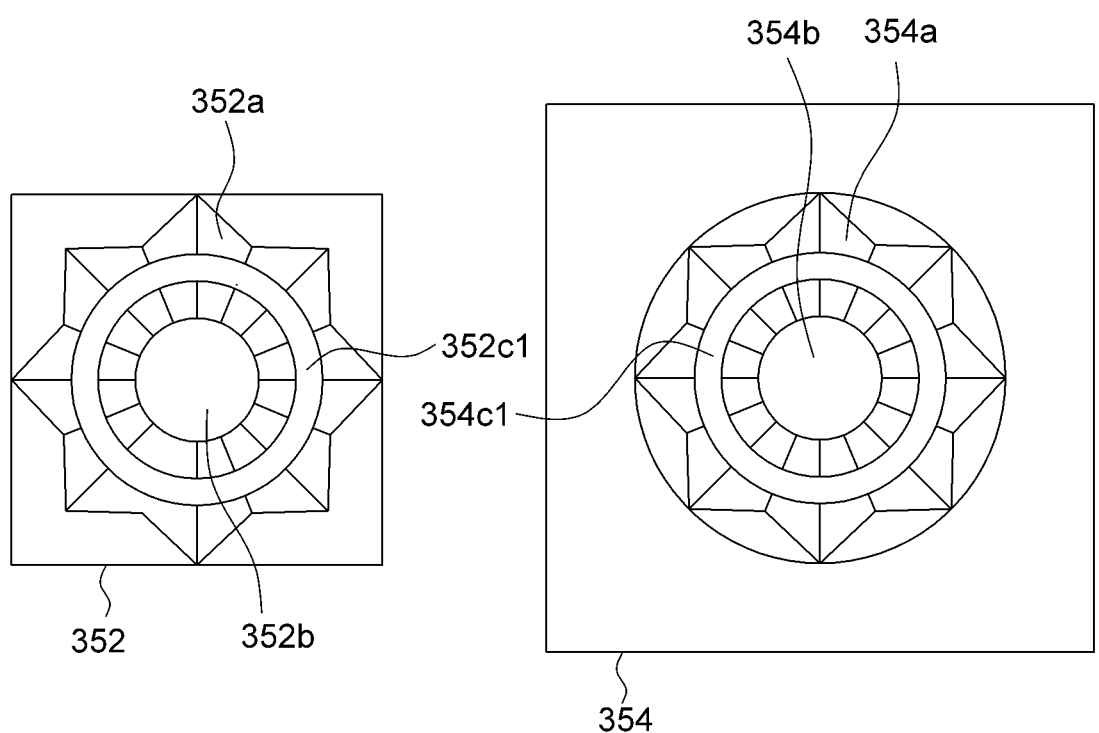
FIG. 6B is a top plan view of a first locking block and a bottom plan view of a second locking block.
Figure 6C:
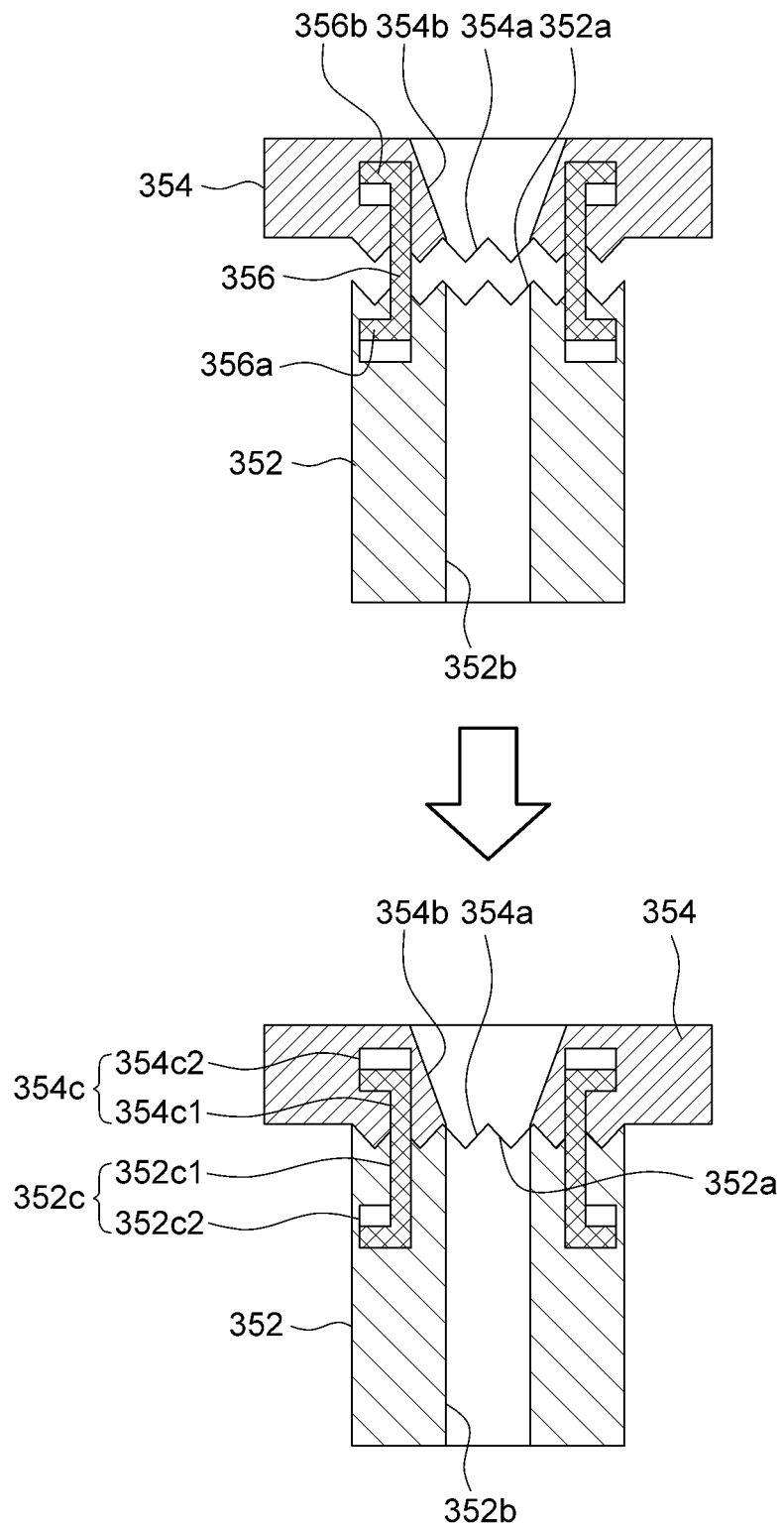
FIG. 6C is a cross-sectional view illustrating the locking member.
Figure 6D:
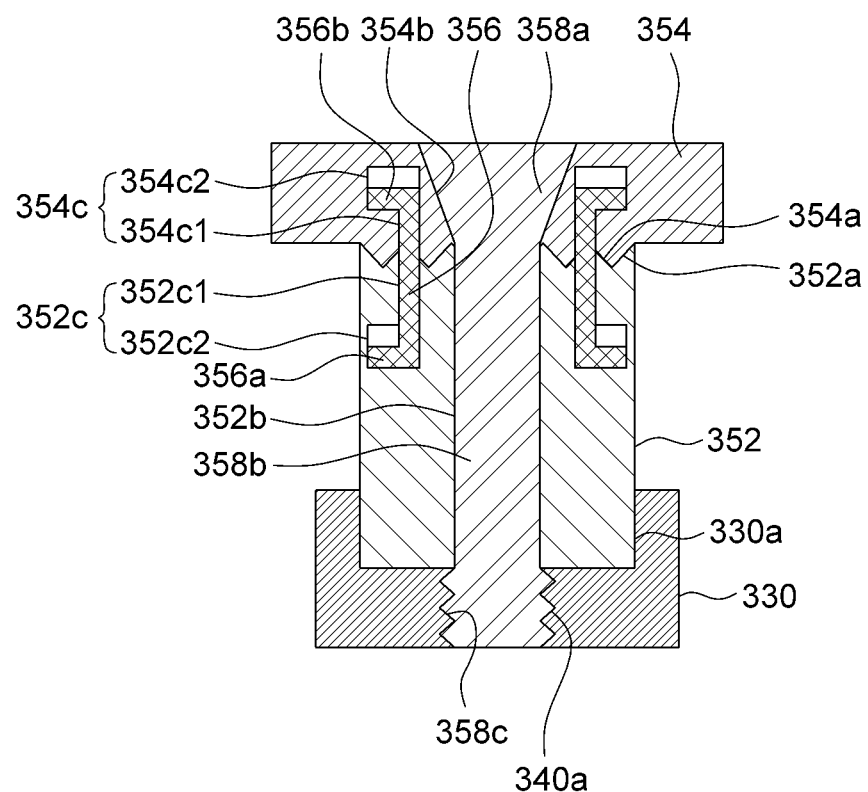
FIG. 6D is a view illustrating a state in which the locking member and the adjustment member are coupled by a fixing screw.

FIG. 6A is a front view illustrating the locking member, and FIG. 6B is a top plan view of a first locking block and a bottom plan view of a second locking block. FIG. 6C is a cross-sectional view illustrating the locking member, and FIG. 6D is a view illustrating a state in which the locking member and the adjustment member are coupled by the fixing screw.

Referring to FIGS. 6A and 6C, the locking member 350 includes a first locking block 352, a second locking block 354, a connection flange 356, and the fixing screw 358. The locking member 350 may be made of a metallic material such as stainless steel or a plastic material. In addition, the locking member 350 may be made of various materials having rigidity and high corrosion resistance.

The first locking block 352 has a hollow cylindrical shape to accommodate the fixing screw 358, and a plurality of first teeth 352*a* may be formed on an upper portion of the first locking block 352 and engage with a plurality of second teeth 354*a* of the second locking block 354. In addition, the first locking block 352 has the first through-hole 352*b* and a first catching groove 352*c*.

The first through-hole 352*b* is formed to accommodate a body 358*b* of the fixing screw 358, and the first through-hole 352*b* communicates with the second through-hole 354*b*.

The first catching groove 352*c* includes a first catching portion 352*c*1 configured to accommodate one end of the connection flange 356, and a second catching portion 352*c*2 configured to accommodate a first protruding portion 356*a* protruding and extending from one end of the connection flange 356.

The first catching portion 352*c*1 extends from one side of the second catching portion 352*c*2. The first catching portion 352*c*1 communicates with a first catching portion 354*c*1 of a second catching groove 354*c* of the second locking block 354.

The second catching portion 352*c*2 has a larger width than the first protruding portion 356*a* of the connection flange 356.

The second locking block 354 has a hollow cylindrical shape to accommodate the fixing screw 358, and the plurality of second teeth 354*a* may be formed on a lower portion of the second locking block 354 and engage with the plurality of first teeth 352*a* of the first locking block 352.

In addition, the second locking block 354 has the second through-hole 354*b* and the second catching groove 354*c*.

The second through-hole 354*b* is formed to accommodate a head 358*a* of the fixing screw 358, and the second through-hole 354*b* communicates with the first through-hole 352*b*.

The second catching groove 354*c* includes the first catching portion 354*c*1 configured to accommodate the other end of the connection flange 356, and a second catching portion 354*c*2 configured to accommodate a second protruding portion 356*b* protruding and extending from the other end of the connection flange 356.

The first catching portion 354*c*1 extends from one side of the second catching portion 354*c*2. The first catching portion 354*c*1 communicates with the first catching portion 352*c*1 of the first catching groove 352*c* of the first locking block 352.

The second catching portion 354*c*2 has a larger width than the second protruding portion 356*b* of the connection flange 356.

The connection flange 356 has a hollow cylindrical shape.

The connection flange 356 is accommodated in the first catching groove 352*c* of the first locking block 352 and the second catching groove 354*c* of the second locking block 354.

The connection flange 356 includes the first protruding portion 356*a* and the second protruding portion 356*b*.

The first protruding portion 356*a* extends and protrudes from one end of the cylindrical connection flange 356 and is accommodated in the second catching portion 352*c*2 of the first catching groove 352*c* of the first locking block 352.

The second protruding portion 356*b* extends and protrudes from the other end of the cylindrical connection flange 356 and is accommodated in the second catching portion 354*c*2 of the second catching groove 354*c* of the second locking block 354.

The fixing screw 358 may be accommodated in the first through-hole 352*b* and the second through-hole 354*b* and include the head 358*a*, the body 358*b*, and the screw thread 358*c*.

The head 358*a* has a head shape of a flat head screw corresponding to a shape of the second through-hole 354*b*.

The body 358*b* extends in a cylindrical shape from one end of the head 358*a*.

The screw thread 358*c* may be formed at an end of the body 358*b*, and the screw thread 358*c* may be screw-coupled to the adjustment member 330.

Hereinafter, a process of locking the first frame 316 and the second frame 326 by using the locking member 350 will be described.

FIG. 6D is a view illustrating a state in which the locking member and the adjustment member are coupled by the fixing screw.

Referring to FIG. 6D, the locking member 350 and the fixing screw 358 are inserted and fixed between the first and second frames 316 and 326 between which the distance is adjusted by the adjustment member 330. Therefore, the first frame 316 and the second frame 326 may be locked in the state in which the distance between the first frame 316 and the second frame 326 is maintained.

More specifically, the first locking block 352 is coupled to the locking groove 330*a* of the adjustment member 330 engaging with the first and second frames 316 and 326 between which the distance is maintained. The second locking block 354 is coupled between the first frame 316 and the second frame 326.

When the fixing screw 358 is inserted into and passes through the first through-hole 352*b* and the second through-hole 354*b* in the state in which the first locking block 352 and the second locking block 354 are coupled to each other, the screw thread 358*c* of the fixing screw 358 comes into contact with the insertion groove 340 of the adjustment member 330. In this state, when the fixing screw 358 is rotated by an adjustment tool (not illustrated) such as a driver or a wrench, the screw thread 358*c* moves along the screw thread 340*a* formed on the insertion groove 340, such that the fixing screw 358 is screw-coupled to the insertion groove 340.

During the process in which the fixing screw 358 is screw-coupled to the insertion groove 340, the first locking block 352 and the second locking block 354 move toward each other, and the connection flange 356 moves in a direction in which the fixing screw 358 is inserted, such that the first protruding portion 356*a* of the connection flange 356 moves to the second catching portion 352*c*2 of the first through-hole 352*b*, and the second protruding portion 356*b* moves to the second catching portion 354*c*2 of the second through-hole 354*b*.

Therefore, when the connection flange 356 moves, the second locking block 354 moves to the first locking block 352, such that the plurality of first teeth 352*a* and the plurality of second teeth 354*a* engage with one another, and the relative rotation between the first and second locking blocks 352 and 354 is restricted.

The first locking block 352 is inserted into the locking groove 330*a* of the adjustment member 330, and the second locking block 354 engaging with the first locking block 352 is inserted and fixed between the first frame 316 and the second frame 326, as illustrated in FIG. 5D. Therefore, the relative rotation between the first and second locking blocks 352 and 354 is restricted, such that the rotation of the adjustment member 330 is restricted by the locking member 350. Therefore, the first frame 316 and the second frame 326 may be locked in the state in which the first frame 316 and the second frame 326 are spaced apart from each other.

Hereinafter, an endoscopic interspinous insert 400 according to yet another embodiment of the present invention will be described. A description of parts identical to the above-mentioned parts of the endoscopic interspinous insert 100 according to the embodiment of the present invention will be omitted, and only parts different from the above-mentioned parts of the endoscopic interspinous insert 100 will be described.

Figure 7A:
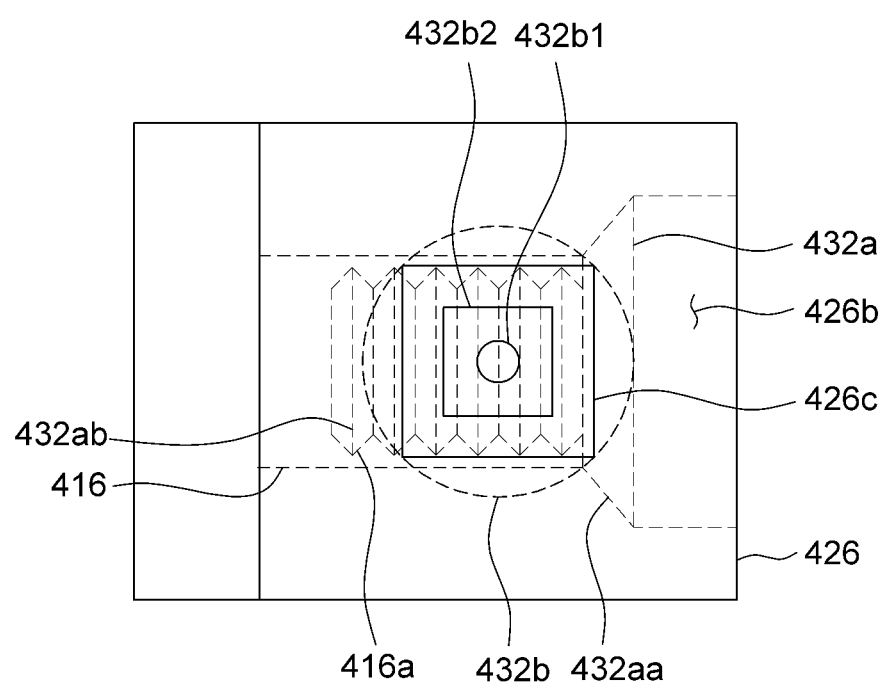
FIG. 7A is a top plan view of a first frame, a second frame, and an adjustment member of an endoscopic interspinous insert according to yet another embodiment of the present invention.
Figure 7B:
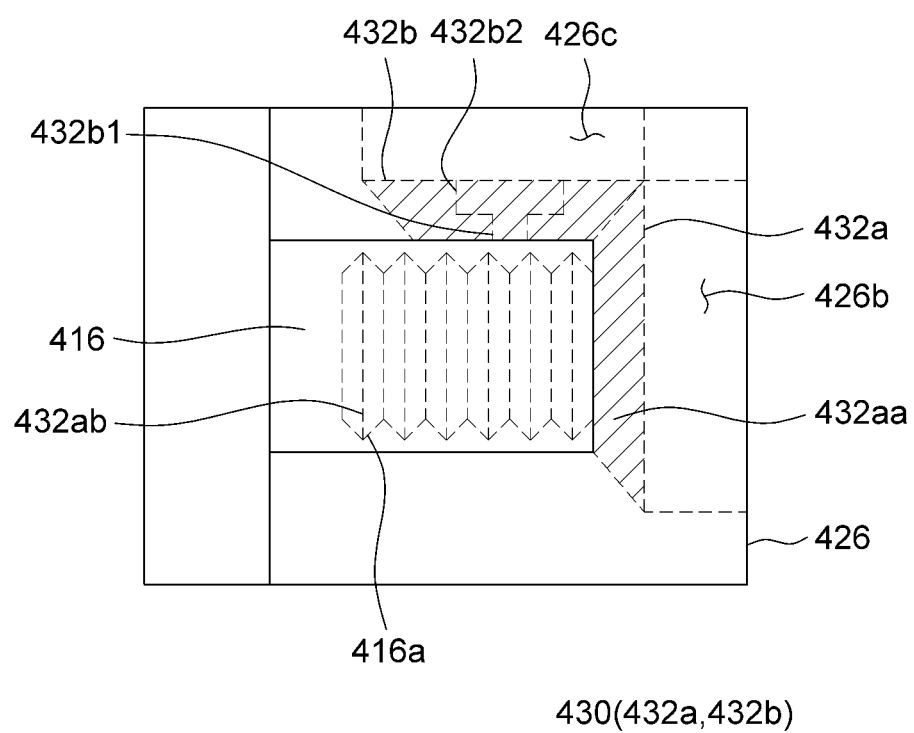
FIG. 7B is a side view of the first frame, the second frame, and the adjustment member of the endoscopic interspinous insert according to the embodiment of the present invention.
Figure 7C:
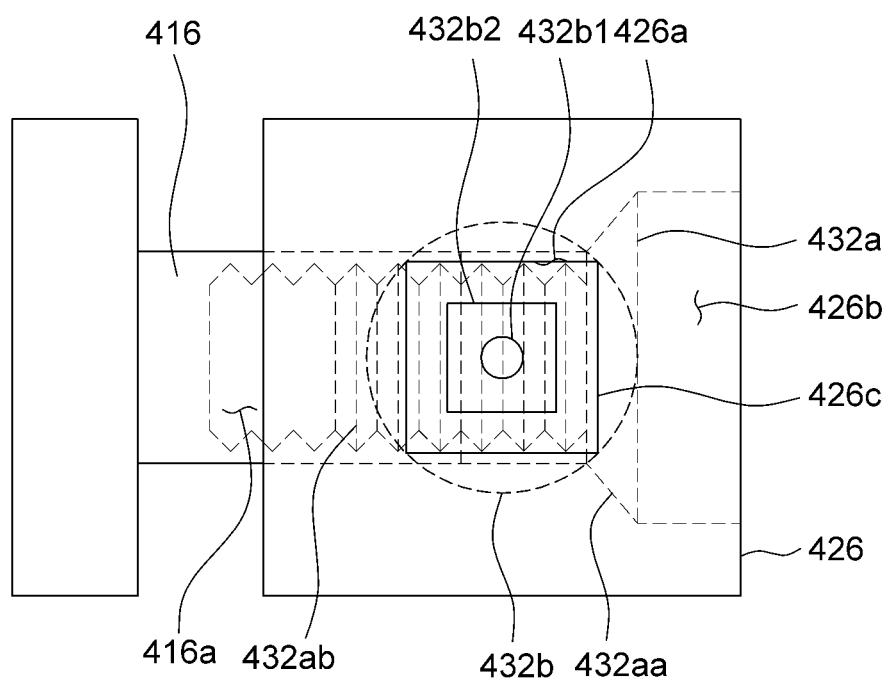
FIGS. 7C and 7D are views illustrating a process of adjusting a distance between the first frame and the second frame.
Figure 7D:
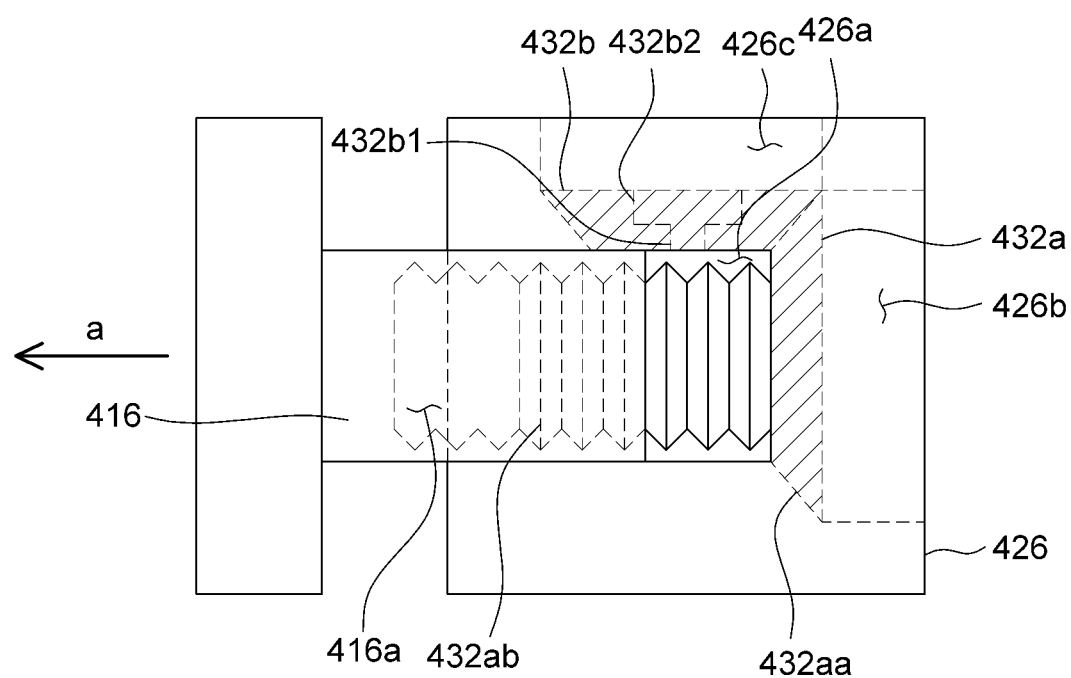

FIG. 7A is a top plan view of a first frame, a second frame, and an adjustment member of an endoscopic interspinous insert according to yet another embodiment of the present invention. FIG. 7B is a side view of the first frame, the second frame, and the adjustment member of the endoscopic interspinous insert according to the embodiment of the present invention. FIGS. 7C and 7D are views illustrating a process of adjusting a distance between the first frame and the second frame.

Referring to FIGS. 7A and 7B, a first frame 416 may have a hollow shape to accommodate an adjustment member 430.

The first frame 416 may be made of a material that is harmless to a human body and may be disinfected. For example, the first frame 416 may be made of a metallic material such as stainless steel or a plastic material. In addition, the first frame 416 may be made of various materials having rigidity and high corrosion resistance.

The first frame 416 has a first accommodation portion 416*a*.

The first accommodation portion 416*a* is formed to accommodate a screw 432*ab* of a screw bevel gear 432*a* of the adjustment member 430.

A second frame 426 may have a hollow shape to accommodate the first frame 416.

The second frame 426 may be made of a material that is harmless to a human body and may be disinfected. For example, the second frame 426 may be made of a metallic material such as stainless steel or a plastic material. In addition, the second frame 426 may be made of various materials having rigidity and high corrosion resistance.

The second frame 426 includes a second accommodation portion 426a, a third accommodation portion 426b, and a fourth accommodation portion 426c.

The second accommodation portion 426a is formed concavely inward to accommodate the first frame 416.

The third accommodation portion 426b accommodates a head portion 432aa of the screw bevel gear 432a of the adjustment member 430.

The fourth accommodation portion 426c accommodates an adjustment bevel gear 432b of the adjustment member 430.

The adjustment member 430 is configured to adjust a distance between the first frame 416 and the second frame 426.

The adjustment member 430 is configured to transmit power and includes the screw bevel gear 432a rotatably accommodated in the third accommodation portion 426b of the second frame 426, and the adjustment bevel gear 432b rotatably accommodated in the fourth accommodation portion 426c of the second frame 426. The adjustment member 430 may be made of a metallic material such as stainless steel or a plastic material. In addition, the adjustment member 430 may be made of various materials having rigidity and high corrosion resistance.

The screw bevel gear 432a is configured to rotate while engaging with the adjustment bevel gear 432b.

The screw bevel gear 432a includes the head 432aa and the screw 432ab.

The head 432aa may be rotatably supported in the third accommodation portion 426b. The screw 432ab may be rotatably supported at a predetermined position in the second accommodation portion 426a of the second frame 426.

The adjustment bevel gear 432b has an insertion groove 432b1 and a locking groove 432b2.

The insertion groove 432b1 is formed concavely from one end of the adjustment bevel gear 432b to an inner side of the adjustment bevel gear 432b and formed in a circular, elliptical, or polygonal shape. In addition, a screw thread (not illustrated) may be formed on an inner surface of the insertion groove 432b1 and coupled to the screw thread 358c formed on the fixing screw 358 of the locking member 350.

When the screw thread 358c provided on the locking member 350 is coupled to the screw thread (not illustrated) of the insertion groove 432b1, the first frame 416 may be locked in a state in which the first frame 416 is spaced apart from the second frame 426.

The locking groove 432b2 is provided at the other end of the adjustment bevel gear 432b and has an elliptical or polygonal shape so that various tools such as a medical driver or a wrench may be inserted.

The locking groove 432b2 is formed concavely from the other end of the adjustment bevel gear 432b to the inner side of the adjustment bevel gear 432b and formed in a polygonal or elliptical shape. When the tool such as a medical driver or a wrench is inserted into the locking groove 432b2 and applies torque, a rotational force is transmitted to the adjustment bevel gear 432b, such that the adjustment bevel gear 432b rotates, and the screw bevel gear 432a engaging with the adjustment bevel gear 432b rotates.

When the screw bevel gear 432a rotates, the first frame 416 moves in the first direction a or a direction opposite to the first direction a, such that the distance between the first frame 416 and the second frame 426 may be adjusted.

Hereinafter, a process of adjusting the distance between the first frame 416 and the second frame 426 and a process of locking the first frame 416 and the second frame 426 by using the locking member 350 will be described.

Referring to FIGS. 7A and 7B, when the tool (not illustrated) such as a medical driver or a wrench is inserted into the locking groove 432b2 of the adjustment bevel gear 432b and applies torque, the adjustment bevel gear 432b rotates in one direction. When the adjustment bevel gear 432b rotates in one direction, the screw bevel gear 432a engaging with the adjustment bevel gear 432b rotates. When the screw bevel gear 432a rotates, the first frame 416 engaging with the screw 432ab of the screw bevel gear 432a moves in the first direction a, such that the distance between the first frame 416 and the second frame 426 increases.

In the state in which the first frame 416 and the second frame 426 are sufficiently spaced apart from each other, the tool (not illustrated) such as a medical driver or a wrench is separated from the locking groove 432b2 of the adjustment bevel gear 432b, the first locking block 352 of the locking member 350 is coupled to the locking groove 432b2, and the second locking block 354 of the locking member 350 is coupled to the fourth accommodation portion 426c of the adjustment bevel gear 432b.

When the fixing screw 358 is inserted into and passes through the first through-hole 352b of the first locking block 352 and the second through-hole 354b of the second locking block 354 in the state in which the first locking block 352 and the second locking block 354 are loosely coupled by the connection flange 356, the screw thread 358c of the fixing screw 358 comes into contact with the insertion groove 432b1 of the adjustment bevel gear 432b. In this state, when the fixing screw 358 is rotated by an adjustment tool (not illustrated) such as a driver or a wrench, the screw thread 358c of the fixing screw 358 moves along the screw thread (not illustrated) formed on the insertion groove 432b1, such that the fixing screw 358 is screw-coupled to the insertion groove 432b1.

During the process in which the fixing screw 358 is screw-coupled to the insertion groove 432b1, the first locking block 352 and the second locking block 354 move toward each other, and the connection flange 356 moves in a direction in which the fixing screw 358 is inserted, such that the first protruding portion 356a of the connection flange 356 moves to the second catching portion 352c2 of the first through-hole 352b, and the second protruding portion 356b moves to the second catching portion 354c2 of the second through-hole 354b.

Therefore, when the connection flange 356 moves, the second locking block 354 moves toward the first locking block 352, such that the plurality of first teeth 352a and the plurality of second teeth 354a engage with one another, and the relative rotation between the first and second locking blocks 352 and 354 is restricted.

The first locking block 352 is fixed to the adjustment bevel gear 432b, and the second locking block 354 engaging with the first locking block 352 is coupled and fixed to the fourth accommodation portion 426c. Therefore, the relative rotation between the first locking block 352 and the second locking block 354 is restricted, such that the rotation of the adjustment bevel gear 432b is restricted by the locking member 350. In addition, the rotation of the screw bevel gear 432a engaging with the adjustment bevel gear 432b is restricted. Therefore, the first frame 416 may be locked in the state in which the first frame 416 is spaced apart from the second frame 426.

Thereafter, when the distance between the first frame 416 and the second frame 426 is required to be adjusted, the fixing screw 358 is separated, the locking member (not illustrated) inserted and fixed into the locking groove 432b2 of the adjustment bevel gear 432b and the fourth accommodation portion 426c of the second frame is separated, and then the adjustment bevel gear 432b is rotated by the tool (not illustrated) such as a medical driver or a wrench, such that the distance between the first frame 416 and the second frame 426 may be adjusted.

Hereinafter, an endoscopic interspinous insert 500 according to still yet another embodiment of the present invention will be described. A description of parts identical to the above-mentioned parts of the endoscopic interspinous insert 100 according to the embodiment of the present invention will be omitted, and only parts different from the above-mentioned parts of the endoscopic interspinous insert 100 will be described.

Figure 8A:
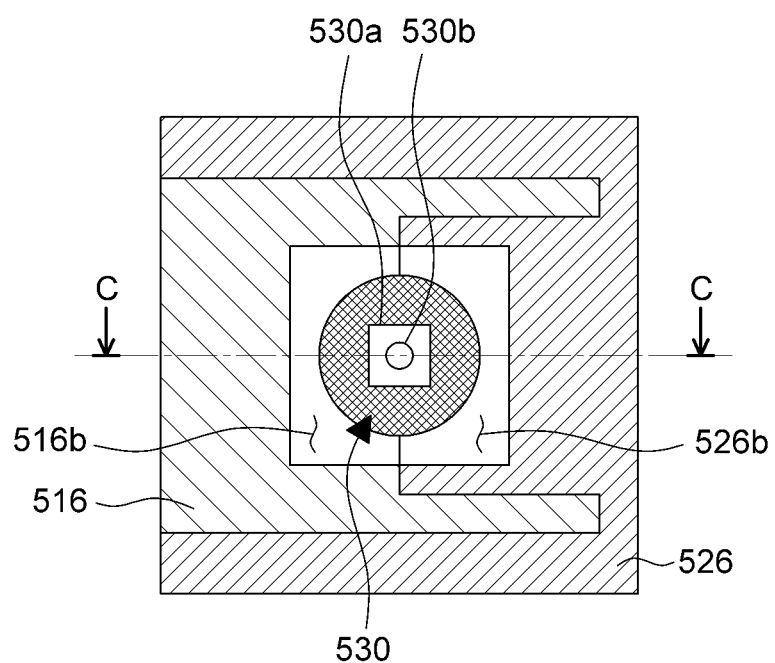
FIG. 8A is a top plan view of a first frame, a second frame, and an adjustment member of an endoscopic interspinous insert according to still yet another embodiment of the present invention.
Figure 8B:
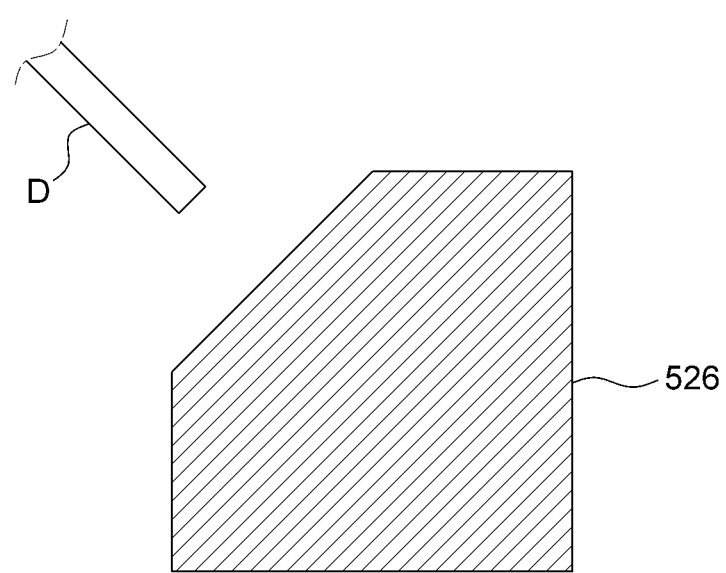
FIG. 8B is a side view of the second frame of the endoscopic interspinous insert according to the embodiment of the present invention.
Figure 8C:
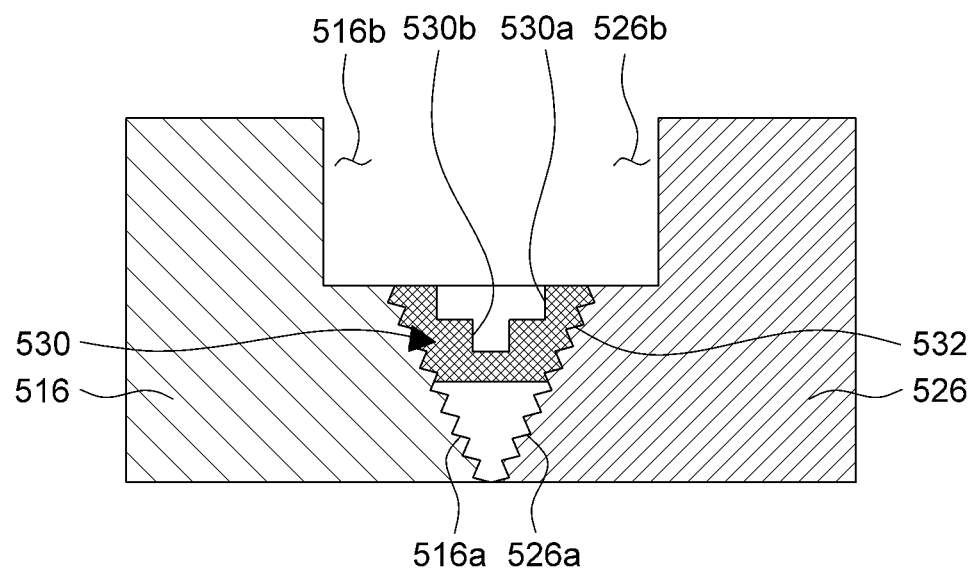
FIG. 8C is a cross-sectional view taken along line C-C in FIG. 8A.
Figure 8D:
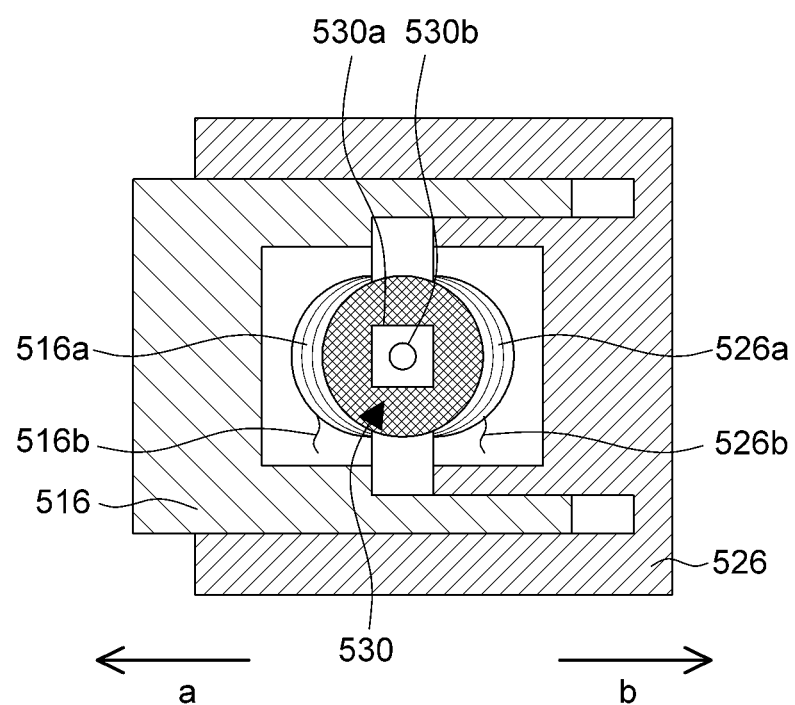
FIG. 8D is a view illustrating a process of adjusting a distance between the first frame and the second frame.

FIG. 8A is a top plan view of a first frame, a second frame, and an adjustment member of an endoscopic interspinous insert according to still yet another embodiment of the present invention. FIG. 8B is a side view of the second frame of the endoscopic interspinous insert according to the embodiment of the present invention. FIG. 8C is a cross-sectional view taken along line C-C in FIG. 8A. FIG. 8D is a view illustrating a process of adjusting a distance between the first frame and the second frame.

Referring to FIGS. 8A to 8D, a first frame 516 may have a hollow shape so that the first frame 516 may be coupled to a second frame 526.

The first frame 516 may be made of a material that is harmless to a human body and may be disinfected. For example, the first frame 516 may be made of a metallic material such as stainless steel or a plastic material. In addition, the first frame 516 may be made of various materials having rigidity and high corrosion resistance.

The first frame 516 includes a first adjustment groove 516a and a first accommodation groove 516b.

The first adjustment groove 516a is formed at one end of the first frame 516 and includes a screw thread provided on an outer peripheral surface thereof. The first adjustment groove 516a is coupled to the second adjustment groove 526a to define a conical shape. That is, the first adjustment groove 516a has a shape having a diameter that gradually decreases in a direction in which the adjustment member 530 is inserted.

The first accommodation groove 516b is angled and formed concavely inward from above to accommodate one end of the second locking block 354 of the locking member 350.

The second frame 526 may have a hollow shape so that the second frame 526 may be coupled to the first frame 516.

The second frame 526 may be made of a material that is harmless to a human body and may be disinfected. For example, the second frame 526 may be made of a metallic material such as stainless steel or a plastic material. In addition, the second frame 526 may be made of various materials having rigidity and high corrosion resistance.

The second frame 526 includes a second adjustment groove 526a and a second accommodation groove 526b.

The second adjustment groove 526a is formed at one end of the second frame 526 and includes a screw thread formed on an outer peripheral surface thereof. The second adjustment groove 526a is coupled to the first adjustment groove 516a to define the conical shape. That is, the second adjustment groove 526a has a shape having a diameter that gradually decreases in the direction in which the adjustment member 530 is inserted.

The second accommodation groove 526b is angled and formed concavely inward from above to accommodate the other end of the second locking block 354 of the locking member 350.

The adjustment member 530 is disposed between the first adjustment groove 516a and the second adjustment groove 526a and has a wedge shape.

The adjustment member 530 includes an insertion groove 530a, a locking groove 530b, and an adjustment screw thread 532. The adjustment member 530 may be made of a metallic material such as stainless steel or a plastic material. In addition, the adjustment member 530 may be made of various materials having rigidity and high corrosion resistance.

The insertion groove 530a is angled and formed concavely from one side of the adjustment member 530 to an inner side of the adjustment member 530 so that various tools such as a medical driver or a wrench may be inserted into the insertion groove 530a.

When the tool such as a medical driver or a wrench is inserted into the insertion groove 530a and applies torque, a rotational force is transmitted to the adjustment member 530, such that the adjustment member 530 rotates. When the adjustment member 530 rotates, the distance between the first and second frames 516 and 526 screw-coupled to the adjustment member 530 increases, and the first frame 516 and the second frame 526 are moved.

In the present embodiment, the insertion groove 530a having a quadrangular shape has been illustrated and described, but the shape of the insertion groove 530a is not limited to the quadrangular shape. The insertion groove 530a may have various shapes such as a circular, elliptical, or polygonal shape in addition to the quadrangular shape.

The locking groove 530b has an elliptical or polygonal shape so that various tools such as a medical driver or a wrench may be inserted into the locking groove 530b. In addition, a screw thread (not illustrated) is formed in the locking groove 530b. The screw thread 358c of the fixing screw 358 may be coupled to the screw thread (not illustrated).

The adjustment screw thread 532 may be provided on the outer peripheral surface of the adjustment member 530 and screw-coupled to the first adjustment groove 516a and the second adjustment groove 526a.

Hereinafter, a process of adjusting a distance between the first frame 516 and the second frame 526 and a process of locking the first frame 516 and the second frame 526 by using the locking member 350 will be described.

Referring to FIGS. 8A to 8D, when the tool (not illustrated) such as a medical driver or a wrench is inserted into the insertion groove 530a of the adjustment member 530 and applies torque, the adjustment screw thread 532 rotates in one direction, and the adjustment member 530 moves to a deep portion between the first frame 516 and the second frame 526. Therefore, the first frame 516 and the second frame 526 move away from each other, the first frame 516 moves in the first direction a, and the second frame 526 moves in the second direction b, such that the distance between the first frame 516 and the second frame 526 increases.

In a state in which the first frame 516 and the second frame 526 are sufficiently spaced apart from each other, the locking member 350 is coupled to the first frame 516, the second frame 526, and the insertion groove 530a, the fixing screw 358 passes through the first through-hole 352b of the first locking block 352 and the second through-hole 354b of the second locking block 354, and the screw thread 358c of the fixing screw 358 is coupled to the screw thread (not illustrated) of the locking groove 530b, such that the movements of the first and second frames 516 and 526 in the first direction a or the second direction b are restricted, and the first frame 516 and the second frame 526 may be locked.

Thereafter, when the distance between the first frame 516 and the second frame 526 is required to be adjusted in accordance with states of the spinous processes S1 and S2, the locking member 350 inserted and fixed into the insertion groove 530a is separated, and then the adjustment member 530 is rotated by the tool such as a medical driver or a wrench, such that the distance between the first frame 516 and the second frame 526 may be adjusted.

Each of the endoscopic interspinous inserts 100, 200, 300, 400, and 500 may further include a pressure sensor (not illustrated) and a communication module (not illustrated). The pressure sensor may sense a pressure of each of the endoscopic interspinous inserts 100, 200, 300, 400, and 500 inserted between the spinous processes. The communication module may be electromagnetically connected to the pressure sensor and transmit an electrical signal, which is received from the pressure sensor, to a device such as an external server or a user terminal through wireless communication.

While the exemplary embodiments of the present invention have been illustrated and described above, the present invention is not limited to the specific exemplary embodiments, and various modifications can of course be made by those skilled in the art to which the present invention pertains without departing from the subject matter of the present invention as claimed in the claims. Further, the modifications should not be appreciated individually from the technical spirit or prospect of the present invention.

What is claimed is:

1. An endoscopic interspinous insert, which is configured to be inserted between adjacent spinous processes, the endoscopic interspinous insert comprising:
   a first support member comprising
      a first support body configured to support one of the adjacent spinous processes,
      a plurality of first support protrusions protruding from two opposite ends of the first support body, and
      a first frame disposed inside the first support body;
   a second support member comprising
      a second support body configured to support the other of the adjacent spinous processes,
      a plurality of second support protrusions protruding from two opposite ends of the second support body, and
      a second frame disposed inside the second support body;
   an adjustment member disposed between the first support member and the second support member and configured to adjust a distance between the first support member and the second support member, the adjustment member comprising
      a screw bevel gear rotatably disposed inside the second frame and coupled to the first support member, and
      an adjustment bevel gear configured to transmit power to the screw bevel gear; and
   a locking member configured to maintain the distance between the first support member and the second support member and to restrict movement of the first support member and the second support member,
   wherein the locking member is coupled to the adjustment bevel gear and the second frame to restrict rotation of the adjustment bevel gear.

2. The endoscopic interspinous insert of claim 1,
   wherein each of the plurality of first support protrusions protrudes from the first support body in a first direction,
   wherein each of the plurality of second support protrusions protrudes from the second support body in a second direction opposite to the first direction, and
   wherein the locking member is further configured to restrict movement of the first support member in the second direction and to restrict movement of the second support member in the first direction.

3. The endoscopic interspinous insert of claim 1,
   wherein the locking member includes a first locking block inserted into the adjustment member and a second locking block inserted between the first support member and the second support member, and
   wherein the locking member is further configured to restrict the rotation of the adjustment bevel gear by restricting the relative rotation between the first locking block and the second locking block.

* * * * *